(12) United States Patent  
VanDeWeghe et al.

(10) Patent No.: US 9,226,809 B2
(45) Date of Patent: Jan. 5, 2016

(54) SURGICAL ARTICLES AND METHODS FOR TREATING URINARY INCONTINENCE

(75) Inventors: Andrew VanDeWeghe, Minnetonka, MN (US); Alan G. Wirbisky, Minnetonka, MN (US); Randall C. Lieser, Minnetonka, MN (US)

(73) Assignee: AMS Research Corporation, Minnetonka, MN (US)

(*) Notice: Subject to any disclaimer, the term of this patent is extended or adjusted under 35 U.S.C. 154(b) by 235 days.

(21) Appl. No.: 13/142,393

(22) PCT Filed: Feb. 10, 2010

(86) PCT No.: PCT/US2010/000325
§ 371 (c)(1),
(2), (4) Date: Jun. 27, 2011

(87) PCT Pub. No.: WO2010/093421
PCT Pub. Date: Aug. 19, 2010

(65) Prior Publication Data
US 2011/0288368 A1    Nov. 24, 2011

Related U.S. Application Data

(60) Provisional application No. 61/151,378, filed on Feb. 10, 2009, provisional application No. 61/151,550, filed on Feb. 11, 2009.

(51) Int. Cl.
*A61F 2/02* (2006.01)
*A61F 2/00* (2006.01)
(Continued)

(52) U.S. Cl.
CPC ......... *A61F 2/0045* (2013.01); *A61B 17/06109* (2013.01); *A61B 2017/00805* (2013.01);
(Continued)

(58) Field of Classification Search
CPC ... A61F 2/0031; A61F 2/0036; A61F 2/0045; A61F 2/005; A61F 2/0054; A61B 2017/00805; A61B 17/06109; A61B 17/06066
USPC .......................................... 600/30
See application file for complete search history.

(56) References Cited

U.S. PATENT DOCUMENTS 2,738,790 A    3/1956  Todt et al.
3,472,232 A   10/1969  Earl
(Continued)

FOREIGN PATENT DOCUMENTS

AU    2002241673    11/2005
CA       2404459     8/2005
(Continued)

OTHER PUBLICATIONS

"We're staying ahead of the curve" Introducing the IVS Tunneller Device for Tension Free Procedures, Tyco Healthcare, 3 pages (2002).
(Continued)

*Primary Examiner* — Jacqueline Cheng
*Assistant Examiner* — Eileen Hyde
(74) *Attorney, Agent, or Firm* — Kagan Binder, PLLC

(57) ABSTRACT

Described are devices, implants and kits for treating incontinence in a male or female. In particular an assembly comprising a multi-piece implant comprising a support portion piece (82) and two extension portion pieces (84) adjustably connected to the support portion piece, and an adjusting tool (92) to allow adjustment of extension portion pieces relative to the support portion piece, is described.

15 Claims, 12 Drawing Sheets

(51) Int. Cl.
*A61B 17/06* (2006.01)
*A61B 17/00* (2006.01)
*A61F 2/30* (2006.01)

(52) U.S. Cl.
CPC ............. *A61B2017/06019* (2013.01); *A61B 2017/06042* (2013.01); *A61F 2002/3055* (2013.01); *A61F 2220/0016* (2013.01); *A61F 2250/0007* (2013.01)

(56) References Cited

U.S. PATENT DOCUMENTS

| | | | |
|---|---|---|---|
| 3,580,313 A | 5/1971 | McKnight | |
| 3,763,860 A | 10/1973 | Clarke | |
| 3,858,783 A | 1/1975 | Kapitanov et al. | |
| 3,995,619 A | 12/1976 | Glatzer | |
| 4,172,458 A | 10/1979 | Pereyra | |
| 4,235,238 A | 11/1980 | Ogiu et al. | |
| 4,441,497 A | 4/1984 | Paudler | |
| 4,509,516 A | 4/1985 | Richmond | |
| 4,548,202 A | 10/1985 | Duncan | |
| 4,632,100 A | 12/1986 | Somers et al. | |
| 4,873,976 A | 10/1989 | Schreiber | |
| 4,932,962 A | 6/1990 | Yoon et al. | |
| 4,938,760 A | 7/1990 | Burton et al. | |
| 4,969,892 A | 11/1990 | Burton et al. | |
| 4,979,956 A | 12/1990 | Silvestrini | |
| 5,013,292 A | 5/1991 | Lemay | |
| 5,013,316 A | 5/1991 | Goble et al. | |
| 5,053,043 A | 10/1991 | Gottesman et al. | |
| 5,085,661 A | 2/1992 | Moss | |
| 5,112,344 A | 5/1992 | Petros | |
| 5,141,520 A | 8/1992 | Goble et al. | |
| 5,149,329 A | 9/1992 | Richardson | |
| 5,188,636 A | 2/1993 | Fedotov | |
| 5,203,864 A | 4/1993 | Phillips | |
| 5,209,756 A | 5/1993 | Seedhom et al. | |
| 5,234,438 A | 8/1993 | Semrad | |
| 5,256,133 A | 10/1993 | Spitz | |
| 5,268,001 A | 12/1993 | Nicholson et al. | |
| 5,269,783 A | 12/1993 | Sander | |
| 5,281,237 A | 1/1994 | Gimpelson | |
| 5,328,077 A | 7/1994 | Lou | |
| 5,337,736 A | 8/1994 | Reddy | |
| 5,354,292 A | 10/1994 | Braeuer et al. | |
| 5,368,595 A | 11/1994 | Lewis | |
| 5,370,650 A | 12/1994 | Tovey et al. | |
| 5,370,662 A | 12/1994 | Stone et al. | |
| 5,376,097 A | 12/1994 | Phillips | |
| 5,383,904 A | 1/1995 | Totakura et al. | |
| 5,403,328 A | 4/1995 | Shallman | |
| 5,439,467 A | 8/1995 | Benderev et al. | |
| 5,474,518 A | 12/1995 | Velazquez | |
| 5,474,543 A | 12/1995 | McKay | |
| 5,520,700 A | 5/1996 | Beyar et al. | |
| 5,520,703 A | 5/1996 | Essig | |
| 5,527,342 A | 6/1996 | Pietrzak et al. | |
| 5,544,664 A | 8/1996 | Benderev et al. | |
| 5,562,689 A | 10/1996 | Green et al. | |
| 5,571,139 A | 11/1996 | Jenkins, Jr. | |
| 5,582,188 A | 12/1996 | Benderev et al. | |
| 5,584,860 A | 12/1996 | Goble et al. | |
| 5,591,163 A | 1/1997 | Thompson | |
| 5,591,206 A | 1/1997 | Moufarrege | |
| 5,611,515 A | 3/1997 | Benderev et al. | |
| 5,628,756 A | 5/1997 | Barker, Jr. et al. | |
| 5,643,320 A | 7/1997 | Lower et al. | |
| 5,647,836 A | 7/1997 | Blake et al. | |
| 5,669,935 A | 9/1997 | Rosenman et al. | |
| 5,674,247 A | 10/1997 | Sohn | |
| 5,683,349 A | 11/1997 | Makower et al. | |
| 5,690,655 A | 11/1997 | Hart et al. | |
| 5,697,931 A | 12/1997 | Thompson | |
| 5,709,708 A | 1/1998 | Thal | |
| 5,725,529 A | 3/1998 | Nicholson et al. | |
| 5,725,541 A | 3/1998 | Anspach, III et al. | |
| 5,741,282 A | 4/1998 | Anspach, III et al. | |
| 5,782,862 A | 7/1998 | Bonutti | |
| 5,842,478 A | 12/1998 | Benderev et al. | |
| 5,860,425 A | 1/1999 | Benderev et al. | |
| 5,873,891 A | 2/1999 | Sohn | |
| 5,899,909 A | 5/1999 | Claren et al. | |
| 5,904,692 A | 5/1999 | Steckel et al. | |
| 5,922,026 A | 7/1999 | Chin | |
| 5,925,047 A | 7/1999 | Errico et al. | |
| 5,944,732 A | 8/1999 | Raulerson et al. | |
| 5,954,057 A | 9/1999 | Li | |
| 5,972,000 A | 10/1999 | Beyar et al. | |
| 5,980,558 A | 11/1999 | Wiley | |
| 5,984,927 A | 11/1999 | Wenstrom, Jr. | |
| 5,988,171 A | 11/1999 | Sohn et al. | |
| 5,997,554 A | 12/1999 | Thompson | |
| 6,007,539 A | 12/1999 | Kirsch et al. | |
| 6,019,768 A | 2/2000 | Wenstrom et al. | |
| 6,027,523 A | 2/2000 | Schmieding | |
| 6,030,393 A | 2/2000 | Corlew | |
| 6,036,701 A | 3/2000 | Rosenman | |
| 6,039,686 A | 3/2000 | Kovac | |
| 6,042,534 A | 3/2000 | Gellman et al. | |
| 6,042,583 A | 3/2000 | Thompson et al. | |
| 6,048,351 A | 4/2000 | Gordon et al. | |
| 6,053,935 A | 4/2000 | Brenneman et al. | |
| 6,056,688 A | 5/2000 | Benderev et al. | |
| 6,099,538 A | 8/2000 | Moses | |
| 6,099,551 A | 8/2000 | Gabby | |
| 6,099,552 A | 8/2000 | Adams | |
| 6,110,101 A | 8/2000 | Tihon et al. | |
| 6,127,597 A | 10/2000 | Beyar et al. | |
| 6,168,611 B1 | 1/2001 | Rizvi | |
| 6,200,330 B1 | 3/2001 | Benderev et al. | |
| 6,241,736 B1 | 6/2001 | Sater et al. | |
| 6,245,082 B1 | 6/2001 | Gellman et al. | |
| 6,264,676 B1 | 7/2001 | Gellman et al. | |
| 6,273,852 B1 | 8/2001 | Lehe et al. | |
| 6,319,272 B1 | 11/2001 | Brenneman | |
| 6,322,492 B1 | 11/2001 | Kovac | |
| 6,328,744 B1 | 12/2001 | Harari et al. | |
| 6,334,446 B1 | 1/2002 | Beyar | |
| 6,382,214 B1 | 5/2002 | Raz et al. | |
| 6,387,041 B1 | 5/2002 | Harari et al. | |
| 6,406,423 B1 | 6/2002 | Scetbon | |
| 6,406,480 B1 | 6/2002 | Beyar et al. | |
| 6,423,072 B1 | 7/2002 | Zappala | |
| 6,423,080 B1 | 7/2002 | Gellman et al. | |
| 6,440,154 B2 | 8/2002 | Gellman et al. | |
| 6,451,024 B1 | 9/2002 | Thompson et al. | |
| 6,454,778 B2 | 9/2002 | Kortenbach | |
| 6,475,139 B1 | 11/2002 | Miller | |
| 6,478,727 B2 | 11/2002 | Scetbon | |
| 6,491,703 B1 | 12/2002 | Ulmsten | |
| 6,502,578 B2 | 1/2003 | Raz et al. | |
| 6,506,190 B1 | 1/2003 | Walshe | |
| 6,530,943 B1 | 3/2003 | Hoepffner et al. | |
| 6,544,273 B1 | 4/2003 | Harari et al. | |
| 6,582,443 B2 | 6/2003 | Cabak et al. | |
| 6,592,515 B2 | 7/2003 | Thierfelder | |
| 6,592,610 B2 | 7/2003 | Beyar | |
| 6,596,001 B2 | 7/2003 | Stormby et al. | |
| 6,599,235 B2 | 7/2003 | Kovac | |
| 6,602,260 B2 | 8/2003 | Harari et al. | |
| 6,612,977 B2 | 9/2003 | Staskin | |
| 6,635,058 B2 | 10/2003 | Beyar et al. | |
| 6,638,210 B2 | 10/2003 | Berger | |
| 6,638,211 B2 | 10/2003 | Suslian et al. | |
| 6,641,525 B2 | 11/2003 | Rocheleau | |
| 6,673,010 B2 | 1/2004 | Skiba et al. | |
| 6,685,629 B2 | 2/2004 | Therin | |
| 6,689,047 B2 | 2/2004 | Gellman et al. | |
| 6,730,110 B1 | 5/2004 | Harari et al. | |
| 6,746,455 B2 | 6/2004 | Beyar et al. | |
| 6,752,814 B2 | 6/2004 | Gellman et al. | |
| 6,802,807 B2 | 10/2004 | Anderson | |
| 6,884,212 B2 | 4/2005 | Thierfelder et al. | |
| 6,908,425 B2 | 6/2005 | Luscombe | |

(56) References Cited

U.S. PATENT DOCUMENTS

| | | |
|---|---|---|
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer |
| 6,936,052 B2 | 8/2005 | Gellman et al. |
| 6,971,986 B2 | 12/2005 | Staskin et al. |
| 6,974,462 B2 | 12/2005 | Sater |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,556 B2 | 7/2006 | Anderson |
| 7,083,637 B1 | 8/2006 | Tannhauser |
| 7,087,059 B2 | 8/2006 | Harari et al. |
| 7,112,171 B2 | 9/2006 | Rocheleau et al. |
| 7,121,997 B2 | 10/2006 | Kammerer et al. |
| 7,131,943 B2 | 11/2006 | Kammerer |
| 7,223,229 B2 | 5/2007 | Inman et al. |
| 7,226,407 B2 | 6/2007 | Kammerer |
| 7,226,408 B2 | 6/2007 | Harai et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,267,645 B2 | 9/2007 | Anderson et al. |
| 7,291,104 B2 | 11/2007 | Neisz et al. |
| 7,297,102 B2 | 11/2007 | Smith et al. |
| 7,303,525 B2 | 12/2007 | Watschke et al. |
| 7,326,213 B2 | 2/2008 | Benderev et al. |
| 7,347,812 B2 | 3/2008 | Mellier |
| 7,351,196 B2 | 4/2008 | Goldmann et al. |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin |
| 7,410,460 B2 | 8/2008 | Benderev |
| 7,413,540 B2 | 8/2008 | Gellman et al. |
| 7,422,557 B2 | 9/2008 | Arnal |
| 7,494,495 B2 | 2/2009 | Delorme et al. |
| 7,500,945 B2 | 3/2009 | Cox |
| 7,517,313 B2 | 4/2009 | Thierfelder et al. |
| 7,527,588 B2 | 5/2009 | Zaddem et al. |
| 7,527,633 B2 | 5/2009 | Rioux |
| 7,547,316 B2 | 6/2009 | Priewe et al. |
| 7,588,598 B2 | 9/2009 | Delorme et al. |
| 7,601,118 B2 | 10/2009 | Smith et al. |
| 7,614,999 B2 | 11/2009 | Gellman et al. |
| 7,621,865 B2 | 11/2009 | Gellman et al. |
| 7,637,860 B2 | 12/2009 | MacLean |
| 7,686,759 B2 | 3/2010 | Sater |
| 7,686,760 B2 | 3/2010 | Anderson et al. |
| 7,691,050 B2 | 4/2010 | Gellman et al. |
| 7,691,052 B2 | 4/2010 | Gellman et al. |
| 7,740,576 B2 | 6/2010 | Hodroff |
| 7,753,839 B2 | 7/2010 | Siegel et al. |
| 7,762,942 B2 | 7/2010 | Neisz et al. |
| 7,828,715 B2 | 11/2010 | Haverfield |
| 8,727,963 B2 * | 5/2014 | Knoll .............................. 600/30 |
| 2001/0000533 A1 | 4/2001 | Kovac |
| 2001/0018549 A1 | 8/2001 | Scetbon |
| 2001/0027321 A1 | 10/2001 | Gellman et al. |
| 2001/0039423 A1 | 11/2001 | Skiba et al. |
| 2001/0041895 A1 | 11/2001 | Beyar et al. |
| 2001/0049467 A1 | 12/2001 | Lehe et al. |
| 2001/0053916 A1 | 12/2001 | Rioux |
| 2002/0007222 A1 | 1/2002 | Desai |
| 2002/0028980 A1 | 3/2002 | Thierfelder et al. |
| 2002/0035369 A1 | 3/2002 | Beyar et al. |
| 2002/0038119 A1 | 3/2002 | Weber et al. |
| 2002/0038132 A1 | 3/2002 | Abrams |
| 2002/0050277 A1 | 5/2002 | Beyar |
| 2002/0055748 A1 | 5/2002 | Gellman et al. |
| 2002/0058959 A1 | 5/2002 | Gellman et al. |
| 2002/0068948 A1 | 6/2002 | Stormby et al. |
| 2002/0077526 A1 | 6/2002 | Kammerer et al. |
| 2002/0082619 A1 | 6/2002 | Cabak et al. |
| 2002/0091373 A1 | 7/2002 | Berger |
| 2002/0095064 A1 | 7/2002 | Beyar |
| 2002/0095163 A1 | 7/2002 | Beyar et al. |
| 2002/0095181 A1 | 7/2002 | Beyar |
| 2002/0107525 A1 | 8/2002 | Harari et al. |
| 2002/0128681 A1 | 9/2002 | Broome et al. |
| 2002/0147382 A1 | 10/2002 | Neisz et al. |
| 2002/0151909 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 | 10/2002 | Neisz |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz |
| 2003/0023138 A1 | 1/2003 | Luscombe |
| 2003/0036676 A1 | 2/2003 | Scetbon |
| 2003/0045774 A1 | 3/2003 | Staskin et al. |
| 2003/0050530 A1 | 3/2003 | Neisz et al. |
| 2003/0065402 A1 | 4/2003 | Anderson et al. |
| 2003/0171644 A1 | 9/2003 | Anderson et al. |
| 2003/0176875 A1 | 9/2003 | Anderson |
| 2004/0015057 A1 | 1/2004 | Rocheleau et al. |
| 2004/0039453 A1 | 2/2004 | Anderson et al. |
| 2004/0193215 A1 | 9/2004 | Harari et al. |
| 2004/0225181 A1 | 11/2004 | Chu et al. |
| 2004/0267088 A1 | 12/2004 | Kammerer |
| 2005/0000523 A1 | 1/2005 | Beraud |
| 2005/0004576 A1 | 1/2005 | Benderev |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0058578 A1 | 3/2006 | Browning |
| 2006/0089524 A1 | 4/2006 | Chu |
| 2006/0089525 A1 | 4/2006 | Mamo et al. |
| 2006/0195007 A1 | 8/2006 | Anderson |
| 2006/0195010 A1 | 8/2006 | Arnal et al. |
| 2006/0195011 A1 | 8/2006 | Arnal et al. |
| 2006/0217589 A1 | 9/2006 | Wan et al. |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0260618 A1 | 11/2006 | Hodroff et al. |
| 2006/0287571 A1 | 12/2006 | Gozzi |
| 2007/0015953 A1 | 1/2007 | MacLean |
| 2007/0078295 A1 | 4/2007 | landgrebe |
| 2007/0173864 A1 | 7/2007 | Chu |
| 2008/0039678 A1 | 2/2008 | Montpetit et al. |
| 2008/0300607 A1 | 12/2008 | Meade et al. |
| 2009/0012353 A1 | 1/2009 | Beyer |
| 2009/0182190 A1 | 7/2009 | Dann |
| 2009/0192347 A1 * | 7/2009 | Davila et al. .................... 600/37 |
| 2009/0221867 A1 | 9/2009 | Ogdahl et al. |
| 2009/0221868 A1 | 9/2009 | Evans |
| 2010/0010631 A1 | 1/2010 | Otte et al. |
| 2010/0094079 A1 | 4/2010 | Inman |
| 2010/0256442 A1 | 10/2010 | Ogdahl et al. |
| 2011/0112357 A1 | 5/2011 | Chapman et al. |
| 2012/0253108 A1 * | 10/2012 | Fischer .......................... 600/30 |

FOREIGN PATENT DOCUMENTS

| | | |
|---|---|---|
| DE | 4220283 C2 | 5/1994 |
| DE | 10211360 | 9/2003 |
| DE | 20016866 | 3/2007 |
| EP | 0650703 A1 | 6/1994 |
| EP | 0643945 A2 | 7/1994 |

(56) References Cited

FOREIGN PATENT DOCUMENTS

| | | |
|---|---|---|
| EP | 0632999 A1 | 1/1995 |
| EP | 1093758 A1 | 4/2001 |
| EP | 1342450 B1 | 9/2003 |
| FR | 2852813 A1 | 1/2004 |
| FR | 285217 | 10/2004 |
| GB | 2268690 A | 1/1994 |
| GB | 2353220 A | 10/2000 |
| SU | 1225547 A1 | 4/1986 |
| WO | WO9310715 A1 | 6/1993 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9842261 A1 | 10/1998 |
| WO | WO9853745 A1 | 12/1998 |
| WO | WO9937216 A1 | 7/1999 |
| WO | WO9937217 A1 | 7/1999 |
| WO | WO9952450 A1 | 10/1999 |
| WO | WO9953844 A1 | 10/1999 |
| WO | WO9958074 A2 | 11/1999 |
| WO | WO9959477 A1 | 11/1999 |
| WO | WO0013601 A1 | 3/2000 |
| WO | WO0030556 A1 | 6/2000 |
| WO | WO0040158 A2 | 7/2000 |
| WO | WO0057796 A1 | 10/2000 |
| WO | WO0074594 A1 | 12/2000 |
| WO | WO0074613 A1 | 12/2000 |
| WO | WO0074633 A2 | 12/2000 |
| WO | WO0230293 A1 | 4/2002 |
| WO | WO0232284 A2 | 4/2002 |
| WO | WO0234124 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO03013392 A2 | 2/2003 |
| WO | WO03017848 A1 | 3/2003 |
| WO | WO03034939 A1 | 5/2003 |
| WO | WO03047435 A1 | 6/2003 |
| WO | WO03068107 A1 | 8/2003 |
| WO | WO03075792 A1 | 9/2003 |
| WO | WO03086205 A2 | 10/2003 |
| WO | WO03092546 A2 | 11/2003 |
| WO | WO03096928 A1 | 11/2003 |
| WO | WO03096929 A1 | 11/2003 |
| WO | WO2004016196 A2 | 2/2004 |
| WO | WO 2004/019786 | 3/2004 |
| WO | WO2004034912 A1 | 4/2004 |
| WO | WO2005004727 A1 | 1/2005 |
| WO | WO2005046511 A2 | 5/2005 |
| WO | WO2005048850 A2 | 6/2005 |
| WO | WO2005079702 A1 | 9/2005 |
| WO | WO2005122954 A1 | 12/2005 |
| WO | WO2006007189 A1 | 1/2006 |
| WO | WO2006007190 A1 | 1/2006 |
| WO | WO2006031879 A1 | 3/2006 |
| WO | WO2006069078 | 6/2006 |
| WO | WO2006108145 A1 | 10/2006 |
| WO | WO2007002012 A1 | 1/2007 |
| WO | WO2007002071 A1 | 1/2007 |
| WO | WO2007014241 A1 | 2/2007 |
| WO | WO2007016083 A1 | 2/2007 |
| WO | WO2007027592 A2 | 3/2007 |
| WO | WO2007059199 A2 | 5/2007 |
| WO | WO2007097994 | 8/2007 |
| WO | WO2007137226 A2 | 11/2007 |
| WO | WO2007146784 A2 | 12/2007 |
| WO | WO2007149348 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |
| WO | WO 2009/075800 | 6/2009 |

OTHER PUBLICATIONS

Advantage A/T™, Surgical Mesh Sling Kit, Boston Scientific, 6 pages (2002).

Benderev, Theodore V., MD, A Modified Percutaneous Outpatient Bladder Neck Suspension System, Journal of Urology, vol. 152, pp. 2316-2320 (Dec. 1994).

Benderev, Theodore V., MD, Anchor Fixation and Other Modifications of Endoscopic Bladder Neck Suspension, Urology, vol. 40, No. 5, pp. 409-418 (Nov. 1992).

Capio™ CL—Transvaginal Suture Capturing Device—Transvaginal Suture Fixation to Cooper's Ligament for Sling Procedures, Boston Scientific, Microvasive®, 8 pages, (2002).

Cook/Ob Gyn®, Urogynecology, Copyright Cook Urological Inc., pp. 1-36 (1996).

Dargent, D. et al., Insertion of a Suburethral Sling Through the Obturator Membrane in the Treatment of Female Urinary Incontinence, Gynecol Obstet Fertil, vol. 30, pp. 576-582 (2002).

Gynecare TVT Tension-Free Support for Incontinence, The tension-free solution to female Incontinence, Gynecare Worldwide, 6 pages, (2002).

IVS Tunneller—A Universal instrument for anterior and posterior intra-vaginal tape placement. Tyco Healthcare, 4 pages (Aug. 2002).

IVS Tunneller—ein universelles Instrument fur die Intra Vaginal Schlingenplastik, Tyco Healthcare, 4 pages (2001).

Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).

Kovac, S. Robert, et al, Pubic Bone Suburethral Stabilization Sling: A Long Term Cure for SUI?, Contemporary OB/GYN, 10 pages (Feb. 1998).

LigiSure Atlas™, Tyco Healthcare, Valleylab®, 2 pages (no date).

Mitek Brochure, Therapy of Urinary Stess Incontinence in Women Using Mitek GIII Anchors, by Valenzio C. Mascio, MD.

Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advaned Surgical Techniques, vol. 9, No. 1 p.

SABRE™ Bioabsorbable Sling, Generation Now, Mentor, 4 pages (May 2002).

SABRE™ Surgical Procedure, Mentor, 6 pages (Aug. 2002).

Sanz, Luis E. et al., Modification of Abdominal Sacrocolpopexy Using a Suture Anchor System, The Journal of Reproductive Medicine, vol. 48, n. 7, pp. 496-500 (Jul. 2003).

Ulmsten, U. et al., An Ambulatory Surgical Procedure Under Local Anesthesia for Treatment of Female Urinary Incontinence, International Urogynecology Journal, vol. 7, pp. 81-86 (May 1996).

Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).

Vesica® Percutaneous Bladder Neck Stabilization Kit, A New Approach to Bladder Neck Suspenison, Microvasive® Boston Scientific Corporation, 4 pages (1995).

Precision Twist, Low Profile design for Precise Anchor Placement, Boston Scientific Microvasive, 2001 2 pp.

Precision Tack, The Precise Approach to Transvaginal Sling Procedures, Boston Scientific, 1998, 4pp.

\* cited by examiner

SURGICAL ARTICLES AND METHODS FOR TREATING URINARY INCONTINENCE

PRIORITY CLAIM

This application claims the benefit from International Application No. PCT/US2010/000325, which was filed on Feb. 10, 2010, which in turns claims priority under 35 USC §119(e) from U.S. Provisional Patent Application having Ser. No. 61/151,378, filed Feb. 10, 2009, by Wirbisky et al., entitled ENHANCED MALE SINGLE-INCISION SLING FOR URINARY INCONTINENCE, and from U.S. Provisional Patent Application having Ser. No. 61/151,550, filed Feb. 11, 2009, by VanDeWeghe, entitled SINGLE INCISION MALE SLING, all of which are incorporated herein by reference in their entireties.

FIELD OF THE INVENTION

The invention relates to apparatus and methods for treating urinary incontinence by use of an implant to support urethral tissue.

BACKGROUND

Men, women, and children of all ages can suffer from urinary incontinence or involuntary loss of urinary control. Their lives are perpetually interrupted by thoughts of ensuring that they have ready access to a restroom. Everyday activities such as attending a theater or sporting event can become unpleasant. Sufferers often begin to avoid social situations in an effort to reduce the stress associated with their condition.

A variety of treatment options are currently available. Some of these include external devices, behavioral therapy (such as biofeedback, electrical stimulation, or Kegel exercises), prosthetic devices, and surgery. Depending on the age, medical condition, and personal preference of a patient, surgical procedures can be used to completely restore continence.

One type of surgical procedure found to be an especially successful treatment option for incontinence in both men and women, is a sling procedure. Sling procedures typically entail surgically implanting a biocompatible implant or "sling" to support the bladder neck or urethra. Sling procedures are discussed in U.S. Pat. Nos. 5,112,344; 5,611,515; 5,842,478; 5,860,425; 5,899,909; 6,039,686; 6,042,534; 6,110,101; 6,478,727; 6,638,211; and PCT Publication Nos. WO 02/39890 and WO 02/069781.

Some "pubomedial" sling procedures involve an abdominal incision and installation of a sling between the rectus fascia in the abdominal region to a position below the urethra, and back again to the rectus fascia. A conventional procedure in females is to surgically place a sling by entering the abdominal cavity through an incision in the patient's pubovaginal region.

In males, one example of a conventional method involves surgical placement of a sling by entering the abdominal cavity through an abdominal incision. Unfortunately, to access the abdominal cavity a surgeon must incise the male patient's abdominal muscles. This procedure is more time consuming and uncomfortable for the male patient.

Other methods for treating pelvic conditions involve installation of a sling below the urethra through incisions made at the inner thigh (e.g., in the perineal skin facing the obturator and in the groin), and using a tissue path extending through the obturator. These procedures can be referred to as "transobturator" methods. See, e.g., U.S. Pat. No. 6,911,003 and Published U.S. Pat. Appl. No. 2003/0171644A1, the entireties of each being incorporated herein by reference.

While abdominal and transobturator methods of treating urinary incontinence can be effective, safe, and long-lasting, there is ongoing effort toward improving these methods.

SUMMARY

The invention relates to methods of treating urinary incontinence in males and females.

Certain embodiments of methods and implants involve placement of a tissue support portion an implant below a urethra, placement of extension portions of the implant at tissue paths that extend from a location to support the urethra in a toward an obturator foramen. A tissue path may extend and end at pelvic fascia without reaching or passing into or through the obturator foramen. In other embodiments a tissue path may extend to the obturator foramen. In still other embodiments the tissue path may extend through an obturator foramen and to an external incision at an inner thigh. The methods can involve two opposing tissue paths, as described, one on each of a left and a right side of the patient.

The implant may involve adjustable extension portions, and the methods may involve adjusting the adjustable extension portions. Alternately or in addition, the implant may be adjusted by use of an adjusting tool that can contact spaced-apart surfaces of an implant to allow contact and manipulation of the two surfaces, simultaneously, by the single tool.

Other embodiments of implants and methods can alternately or additionally involve the use of "small-diameter" insertion tools (e.g., needles) that can be passed through a tissue path (that traverses the obturator foramen) with reduced trauma to the patient.

Still other embodiments of methods of treating incontinence in a male or female patient can involve the use of a urethra-positioning tool that can position a urethra in a location and manner to improve continence, followed by fixing the urethra in that position.

In one aspect, the invention relates to an assembly for treating urinary incontinence. The assembly includes a multi-piece implant having a support portion piece and two extension portion pieces, and an adjusting tool. The support portion piece includes a tissue support portion sized and shaped for placement to support a urethra, and the extension portion pieces each include a proximal end, a distal end, and a tissue fastener. The first extension portion piece is adjustably connected to the support portion piece at a first adjustable connection. The second extension portion piece is adjustably connected to the support portion piece at a second adjustable connection. The adjusting tool includes two adjusting surfaces, the two adjusting surfaces being capable of simultaneously engaging the support portion piece to allow adjustment of a position of the extension portion piece relative to the support portion piece at the first adjustable connection, and adjustment of a position of the second extension portion piece relative to the support portion piece at the second adjustable connection.

In a related aspect, the assembly can be used to treat urinary incontinence according to methods that involve: providing the assembly; creating a medial incision in the patient; dissecting from the medial incision to tissue below a urethra; placing the tissue support portion to contact tissue to support the urethra; placing a distal end of the first extension portion in a tissue path extending toward a first obturator foramen of the patient; placing a distal end of the second extension portion in a tissue path extending toward a second obturator foramen of the patient; connecting the first extension portion piece with the support portion piece at the first adjustable connection; connecting the second extension portion piece with the support portion piece at the second adjustable connection; engaging the adjusting tool with the support portion piece, and adjusting a position of the support portion piece relative to first and second extension portion pieces.

In another aspect, the invention relates to an implant for treating urinary incontinence. The implant includes a tissue support portion sized and shaped for placement to support a urethra; two extension portions, each extension portion extending from an end of the tissue support portion; and a tissue fastener at each extension portion. Each extension portion has an adjustable length between the tissue support portion and the tissue fastener.

In a related aspect the invention relates to a method of treating urinary incontinence in a patient using this type of implant. The method includes: providing the implant; creating a medial incision in the patient; dissecting from the medial incision to tissue below a urethra; placing the tissue support portion to support the urethra; placing the tissue fastener at the first extension portion in a tissue path extending toward a first obturator foramen of the patient; placing the tissue fastener at the second extension portion in a tissue path extending toward a second obturator foramen of the patient; and adjusting a length of an extension portion.

In another aspect the invention relates to an assembly for treating urinary incontinence in a patient. The assembly includes an implant comprising a tissue support portion and two extension portions, and an insertion tool. The insertion tool has a small-diameter needle having a diameter of less than 0.09 inch, a radius of curvature at a tip at one end of the needle that is less than 0.015 inch, and a length to extend between a medial incision in a patient, and a lateral incision in a patient adjacent to an obturator foramen.

In a related aspect, the invention involves method of treating urinary incontinence, by using this assembly. The method includes: providing the assembly; creating a medial incision in the patient; dissecting from the medial incision to tissue below a urethra; placing the tissue support portion to support the urethra; attaching the extension portion to the small diameter needle; using the small-diameter needle, passing the extension portion between the medial incision and an external location adjacent to an obturator foramen, the needle and extension portion passing through an obturator foramen.

In another aspect the invention relates to a urethra-positioning tool having an elongate shaft capable of being inserted through a meatus and into a urethra to adjust a positioning of the urethra.

A related aspect of the invention relates to a method of treating urinary treating incontinence using the urethra-positioning tool. The method includes: providing the urethra-positioning tool; inserting the shaft through a meatus and into a urethra; using the urethra-positioning tool to approximate the urethra into a position to treat the incontinence; and fixing the urethra in the position to treat incontinence.

DETAILED DESCRIPTION

Figure 1A:
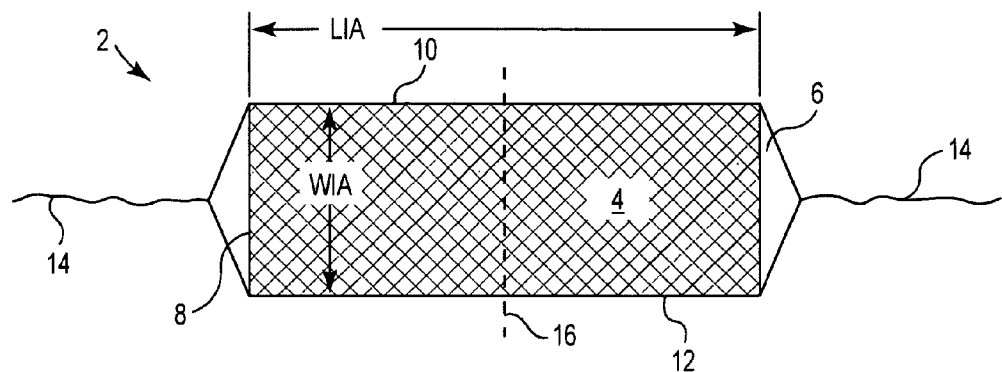
FIGS. 1A, 1B, 1C, and 1D illustrate exemplary features of implants, support portion pieces, and tissue support portions of implants as described.

The present invention is directed to surgical instruments, assemblies, and implantable articles for treating urinary incontinence in a male or female, including stress urinary incontinence (SUI), as well as related methods Described are various features of surgical implants, surgical tools, surgical systems, surgical kits, and surgical methods, useful for installing implants for treating incontinence. An implant can be implanted in a male or a female to treat a condition such as urge incontinence, mixed incontinence, overflow incontinence, functional incontinence, and the like.

An implant can include a tissue support portion (or "support portion") that can be used to support a urethra. Supporting a "urethra" refers to supporting tissue that includes the urethra (which can refer to the bladder neck) and that can optionally include tissue adjacent to a urethra such as bulbospongiosus muscle, corpus spongiosum, or both. According to various methods, for example, a support portion of an implant may either be placed below bulbospongiosus muscle to support both bulbospongiosus muscle and corpus spongiosum (along with the urethra), or alternately bulbospongiosus muscle may be dissected and a support portion of an implant may be placed to contact corpus spongiosum tissue (to support the urethra). During use, the tissue support portion is typically placed below the urethra, e.g., in contact with corpus spongiosum tissue, and can optionally be attached to tissue, such as with a suture.

An implant can additionally include one or more extension portion (otherwise known as "end" portions or "arms") attached to the tissue support portion. Normally, for treating incontinence, an implant can include two opposing extension portions. Extension portions are elongate pieces of material (e.g., mesh, suture, or biologic material) that extend from the tissue support portion and either are or can be connected to the tissue support portion, and are useful to attach to anatomical features or "supportive tissue" in the pelvic region (e.g., using a self-fixating tip) to thereby provide support for the tissue support portion and the supported tissue. Generally for treating incontinence, two extension portions can extend from the opposite ends of a tissue support portion as elongate "ends," "arms," or "extensions," and may attach to supportive tissue in the pelvic region by extending through a tissue path to an internal anchoring point (see, e.g., Applicant's copending U.S. patent application Ser. No. 12/223,846, filed Aug. 8, 2008, by Ogdahl, entitled SURGICAL ARTICLES AND METHODS FOR TREATING PELVIC CONDITIONS, the entirety of which is incorporated herein by reference), or may extend to an external incision, such as through an obturator foramen and through an external incision at a groin or inner thigh (see, e.g., Applicant's copending United States Patent Publication Number US 2006/0287571, the entirety of which is incorporated herein by reference).

In exemplary uses, each extension portion can extend from the location of attachment to the tissue support portion, through pelvic tissue, and optionally attached to supportive tissue within the pelvic region; optionally the extension portion can also extend to and through an external incision. For certain procedures (that do not involve external incisions) the supportive tissue can be tissue adjacent to the urethra such as pelvic fascia; tissue between the urethra and an obturator foramen such as pelvic fascia; or tissue of an obturator foramen such as obturator fascia, obturator internus muscle, obturator membrane, obturator externus muscle, etc. For alternate procedures, sometimes referred to as "transobturator"-type procedures, an extension portion can be sized to extend from the tissue support portion, through an obturator foramen, and to then exit through an external incision in a region of a groin or inner thigh, adjacent to an obturator foramen.

An implant may include portions, pieces, or sections that are synthetic or of biological material (e.g., porcine, cadaveric, etc.). Extension portions may be, e.g., a synthetic mesh such as a polypropylene mesh, a suture, a biodegradable suture, etc. The tissue support portion may be synthetic (e.g., a polypropylene mesh) or biologic. Examples of implant products that may be similar to those useful according to the present description, include those sold commercially by American Medical Systems, Inc., of Minnetonka Minn., under the trade names Apogee® and Perigee® for use in treating pelvic prolapse (including vaginal vault prolapse, cystocele, enterocele, etc.), and Sparc®, Bioarc®, and Monarc® for treating urinary incontinence.

An example of a particular type of pelvic implant is the type that includes supportive portions including or consisting of a tissue support portion and two opposing extension portions extending from the tissue support portion. An implant that has exactly two extension portions can be of the type useful for treating urinary incontinence. The term "supportive portions" refers to portions of an implant that function to support tissue after the implant has been implanted, and specifically includes extension portions and tissue support portions, and does not include optional or appurtenant features of an implant such as a sheath, tissue fastener, or self-fixating tip or other type of connector for attaching the implant to an insertion tool.

A preferred sling for placement against a corpus spongiosum for treatment of urinary incontinence in a male patient may optionally and preferably include a widened central support, for increased contact and frictional engagement with the corpus spongiosum. According to exemplary embodiments, the sling can be tensioned to approximate corpus spongiosum proximally. A widened tissue support portion can provide improved mechanical and frictional engagement between the tissue support portion and the corpus spongiosum. A widened tissue support portion provides a larger area of contact between the implant and corpus spongiosum, and can have a reduced tendency to fold or deform upon tensioning of the implant. A suture can be used to attach the tissue support portion to the corpus spongiosum to further improve the area of contact and prevent folding, such as at a location on the anterior side of the tissue support portion. A suture may also be useful to prevent movement of the tissue support portion relative to the corpus spongiosum during or after installation or tensioning. An implant for treating male urinary incontinence can optionally and preferably have a widened tissue support portion, as discussed, for example, in Assignee's copending United States Patent Publication Number US 2006/0287571 and U.S. Pat. No. 7,422,557, the entireties of these applications being incorporated herein by reference.

Dimensions of a tissue support portion can be dimensions useful to support urethra tissue for treating incontinence. A tissue support portion can be of sufficient length to support and optionally partially surround a urethra or urethra-supporting tissue. A width of a tissue support portion may optionally and preferably be greater than a width of extension portions and can be sufficiently wide to increase contact area and frictional forces between a tissue support portion and a tissue in contact with the tissue support portion. Exemplary lengths of a tissue support portion can be in the range from 0.5 to 2 inches, such as from 0.75 to 1.5 inches. Exemplary widths of a tissue support portion can be in the range from 0.4 or 0.5 to 4 centimeters, such as from 1 to 2.5 or 3 centimeters. (A tissue support portion may be part of a support portion piece that includes the tissue support portion and optionally some amount of opposing extension portions extending from ends of the tissue support portion (see, e.g., FIGS. 1D, 2A, 2B, 3A, and 4A); when considering dimensions of these implants, the length of the support portion piece may be considered to include a length of the tissue support portion and additionally a length of any portion of the support portion piece that is considered to be an extension portion.)

Dimensions of extension portions according to the invention can allow the extension portion to reach between a tissue support portion placed to support a urethra (at an end of the extension portion connected to the tissue support portion) and, either: a location at which the distal end of the extension portion attaches to supportive tissue at or about the pelvic region; or through an obturator foramen and to an external incision at a groin or inner thigh, adjacent to the obturator foramen.

According to certain methods and implants, a distal end of an extension portion, according to certain embodiments of the invention, can include a self-fixating tip that can be attached directly to pelvic tissue such as pelvic muscle, ligament, or tendon. The length of the extension portion, therefore, can be in a range that allows placement of a tissue support portion as desired to support pelvic tissue, while the self-fixating tip is installed in pelvic tissue. Exemplary lengths of an extension portion for these embodiments, measured for example between a connection or boundary between the extension portion and the tissue support portion, and a distal end of the extension portion, can be, e.g., from 0.5 to 2.75 inches, preferably from 1.0 to 2.25 inches, and the length can optionally and preferably be adjustable.

As described elsewhere herein, a length of an extension portion can optionally be fixed (i.e., the extension portion does not include any form of length-adjusting mechanism). Alternate embodiments of implants of the invention may include adjustment or tensioning mechanisms that allow a physician to alter the length of an extension portion before, during, or after implantation.

Examples of various exemplary tissue support portion embodiments are illustrated at FIGS. 1A, 1B, 1C, 1D, and FIG. 8.

As shown at FIG. 1A, implant 2 includes tissue support portion 4 having ends 6 and 8, anterior and posterior sides 10 and 12, and connects to two opposing extension portions 14. Tissue support portion 4 is a mesh, and extension portions 14 are sutures, which may be absorbable. Extension portions 14 are illustrated to be sutures of fixed (non-adjustable) length. Optionally, however, in use, tissue fasteners or self-fixating tips (not shown) may be loosely or adjustable attached to each of extension portions 14 (as illustrated at FIG. 1D). Implant 2 can be placed in a patient to support a urethra midline 16 (a location half-way between ends 6 and 8), and extension portions 14 can be extended to supportive tissue such as at fascia or an obturator foramen, or can extend through an obturator foramen and then through an external incision adjacent to an obturator foramen. Length L1A can be any useful length such as a length in the range from 0.5 to 2 inches. Width W1A can be any useful width, such as a width in the range from 0.4 to 2.5 inches.

Figure 1B:
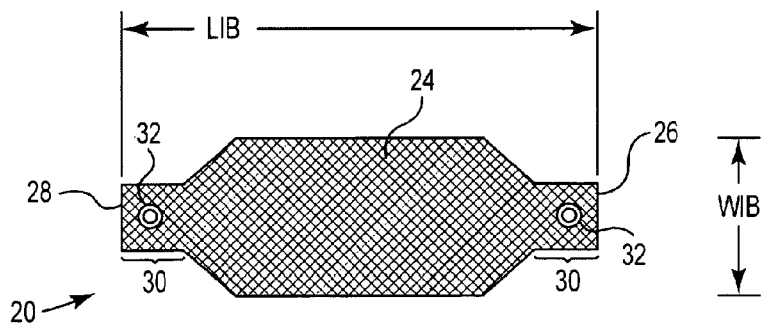

As shown at FIG. 1B, support portion piece 20 includes tissue support portion 24 (mesh) having ends 26 and 28 (alternately, the opposing "tabs" 30 could be considered to be part of an extension portion of the implant). Apertures 32 can be reinforced apertures or grommets that engage an extension portion piece (not shown) of the implant. Apertures or grommets 32 may be "one-way" grommets that allow movement of an extension portion piece through the aperture in one direction, or that frictionally engage an extension portion piece to resist movement in at least one direction. Apertures or grommets 32 are shown to be circular, and as such would receive a circular or deformable extension portion piece, but may alternately be of another shape such as square or rectangular. Length L1B can be any useful length, such as from 0.5 to 2 inches; Width W1B can be any useful width, such as a length in the range from 0.4 to 2.5 inches.

Figure 1C:
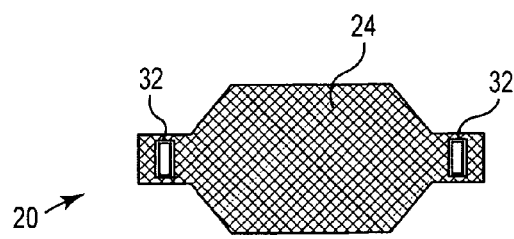
Figure 1D:
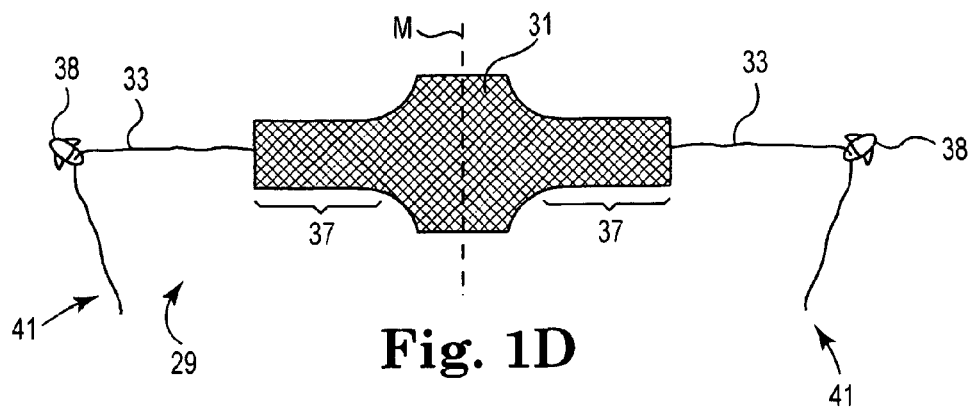
Figure 3A:
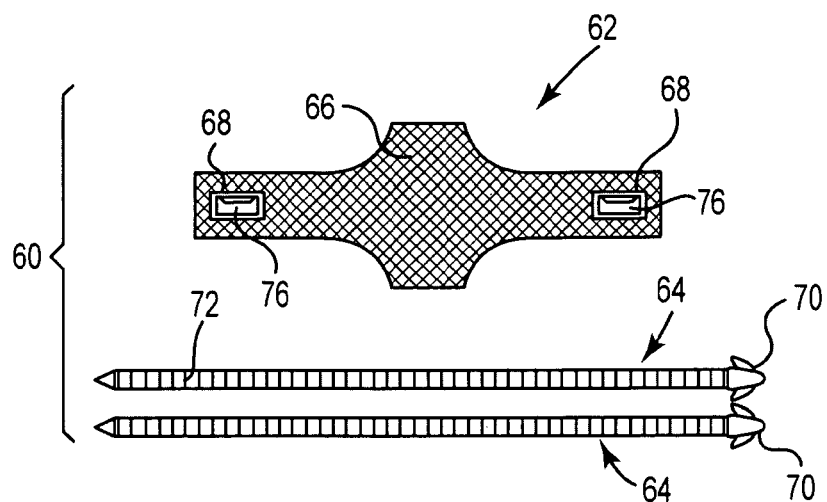
FIGS. 3A, 3B, and 3C illustrate exemplary features of systems, implants, and adjustable connections, as described.

Support portion piece 20 of FIG. 1C is similar to support portion piece 20 of FIG. 1B, modified to include apertures or grommets 32 having a reinforced rectangular perimeter, or "rectangular grommet." Rectangular grommets 32 are shown to have "vertical" slots extending from front to back of support portion piece 20, but may also have "horizontal" slots extending from end to end of support portion piece 20 (see FIG. 3A.

FIG. 1D shows implant 29 that includes tissue support portion 31 (mesh) (opposing "tabs" 37 could optionally be considered to be part of the tissue support portion or as part of an extension portion of the implant). Sutures 33 form extension portions. Self-fixating tips 38 are located on sutures 33, and can be moved along the lengths of sutures 33 to adjust a distance between self-fixating tips 38 and tissue support portion 31 or midline "M." In use, tissue support portion 31 can be placed below a male or female urethra to support the urethra for treating urinary incontinence. Each of self-fixating tips 38 can be passed through a medial incision (using an insertion tool) and implanted at tissue between the urethra and the patient's opposing obturator foramen (e.g., secured to opposing obturator foramen), preferably without creating lateral incisions at opposing inner thighs (adjacent to each obturator foramen). Once the two self-fixating tips are affixed to supportive tissue, distal (or "free") ends 41 of sutures 33 can be pulled medially to adjust the placement of tissue support portion 31 and tension of sutures 33. Optionally (not illustrated), extension portions (e.g., tabs 37 or a portion thereof) can include one or more tissue fastener.

Figure 8:
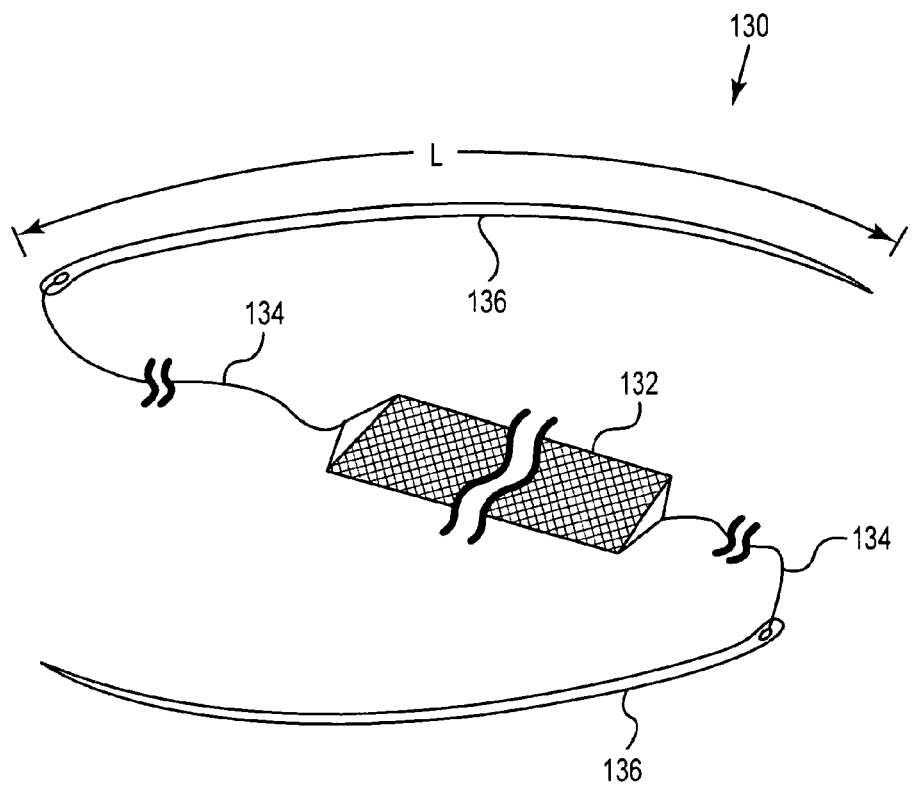
FIGS. 8 and 9 illustrate exemplary features of systems, implants, support portion pieces, and small-diameter insertion tools, as described.

FIG. 8 shows implant 130 that includes tissue support portion 132 (mesh) and two opposing extension portions in the form of sutures 134. Small-diameter needles 136 are attached (e.g., by knots or other mechanical or adhesive connection) at distal ends of each sutures 134.

Implants as described can include a tissue fastener at a distal end or a distal portion of an extension portion, which is the end or portion not attached to a tissue support portion. (The term "distal" as used herein when referring to an extension portion is the end or portion away from a connection to a tissue support portion.)

A tissue fastener at a distal end or portion of a an extension portion can be any of various types, including: a self-fixating tip that is inserted into soft tissue and frictionally retained; soft tissue anchors; biologic adhesive; a soft tissue clamp that can generally include opposing, optionally biased, jaws that close to grab tissue; and opposing male and female connector elements that engage to secure an end of an extension portion to tissue. (See International Patent Application No. PCT/US2007/014120, entitled "Surgical Implants, Tools, and Methods for Treating Pelvic Conditions, filed Jun. 15, 2007; U.S. patent application Ser. No. 12/223,846, filed Aug. 8, 2008, entitled SURGICAL ARTICLES AND METHODS FOR TREATING PELVIC CONDITIONS; U.S. patent application Ser. No. 12/669,099, filed Jan. 14, 2010, entitled PELVIC FLOOR TREATMENTS AND RELATED TOOLS AND IMPLANTS; and WO 2009/075800, the entireties of which are incorporated herein by reference.) An implant may also have one or more extension portion that does not include a tissue fastener, for example if the distal end is designed to be secured to tissue by other methods (e.g., suturing), or is intended to pass through and obturator foramen and an external incision, in which case the extension portion may optionally include a connector, dilator, or dilating connector, which connects to an elongate tool that can be used to either push or pull the connector, dilator, or dilating connector through a tissue path to an external incision.

A tissue fastener on an extension portion can be placed at and secured within internal tissue of the pelvic region to support the implant and urethra that is supported by the implant. For example a tissue fastener can be placed at muscle tissue of an obturator foramen (e.g., obturator internus muscle, obturator membrane, obturator externus muscle, fascia), or at tissue located between a urethra and an obturator foramen, e.g., pelvic fascia.

One embodiment of a tissue fastener is a self-fixating tip. A "self-fixating tip" in general can be a structure (sometimes referred to as a soft tissue anchor) connected at a distal end of an extension portion (or extension portion piece) that can be implanted into soft tissue (e.g., muscle, fascia, ligament, etc.) in a manner that will maintain the position of the self-fixating tip and support the attached implant. Exemplary self-fixating tips can also be designed to engage an end of an insertion tool (e.g., elongate needle, elongate tube, etc.) so the insertion tool can be used to push the self-fixating tip through and into tissue for implantation, preferably also through a medial incision to reach the interior of the pelvic region, e.g., at a location of an obturator foramen. The insertion tool may engage the self-fixating tip at an internal channel of the self-fixating tip, at an external location such as at an external surface of the base, at a lateral extension, or otherwise as desired, optionally in a manner to allow the insertion tool to push the self-fixating tip through an incision in a patient and through and into supportive tissue.

Exemplary self-fixating tips can include one or more lateral extensions that allow the self-fixating tip to be inserted into soft tissue and to become effectively anchored in the tissue. A lateral extension may be moveable or fixed. The size of the self-fixating tip and optional lateral extensions can be useful to penetrate and become anchored into the tissue. Exemplary self-fixating tips are described in Assignee's copending international patent application PCTUS2007/004015, filed Feb. 16, 2007, titled Surgical Articles and Methods for Treating Pelvic Conditions, the entirety of which is incorporated herein by reference. Other structures may also be useful.

According to exemplary embodiments, a self-fixating tip can have structure that includes a base having a proximal base end and a distal base end. The proximal base end can be connected (directly or indirectly, such as by a connective suture) to a distal end of an extension portion. The base extends from the proximal base end to the distal base end and can optionally include an internal channel extending from the proximal base end at least partially along a length of the base toward the distal base end. The optional internal channel can be designed to interact with (i.e., engage) a distal end of an insertion tool to allow the insertion tool to be used to place the self-fixating tip at a location within pelvic tissue of the patient. Embodiments of self-fixating tips also include one or more lateral extension extending laterally (e.g., radially) from the base, such as from a location between the proximal end and the distal end, from a location at the distal base end, or from a location at the proximal base end.

A self-fixating tip can be made out of any useful material, generally including materials that can be molded or formed to a desired structure and connected to or attached to a distal end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA.

Optionally, an implant can include a tissue fastener at a location of a tissue support portion, or at a location along a length of an extension portion. This form of tissue fastener, sometimes referred to as a "tissue fastener" can be in the form of a reinforced (e.g., by coating, heat treating, or a reinforcing weave or strip) edge extensions, multiple layers of mesh and edge extensions in an extension portion, etc., as described, for example, at Applicant's copending U.S. Pat. No. 7,422,557, and Applicant's copending United States Patent Publication Numbers US 2006/0195011, US 2006/0195007, and US 2006/0195010, all of which are incorporated herein by reference.

Other tissue fastener can be structure that is added to a mesh or other type of tissue support portion or extension portion to increase friction between the implant (e.g., tissue support portion or extension portion) and adjacent tissue, to prevent movement after placement of the implant; i.e., to improve short-term or long-term fixation of the extension portion within tissue. Examples of tissue fastener include relatively rigid structures such as metal, plastic, or other polymeric or non-polymeric structure that may be shaped to frictionally engage soft tissue, for example to include a tine, hook, chevron, barb, arrow, etc., combinations thereof, or any structure added to an edge or surface of an extension portion to improve fixation within tissue. The structure can have any shape or form that will increase frictional force between the implant and adjacent tissue, such as one or multiple pointed surface directed along a length of an extension portion, toward the tissue support portion, and extending away from a surface or edge of the implant (e.g., extension portion). The tissue fastener can be secured to a surface or edge of an extension portion by adhesive, thermoforming, insertion into a weave of a mesh, or any other fashion that will secure the tissue fastener to increase frictional resistance between the extension portion and adjacent tissue.

The tissue fastener can be located at a position of an implant that will result in the tissue fastener being located at supportive tissue such as muscle or fascia when the implant is placed with a midline of the tissue support portion being located below a urethra. For example, a tissue fastener may be located on a tissue support portion or an extension portion of an implant, e.g., as close as 2 or 3 centimeters from a midline of a tissue support portion, and up to a distance that reaches tissue of an obturator foramen when the midline is located below a urethra, e.g., up to 7 centimeter from the midline.

Figure 2A:
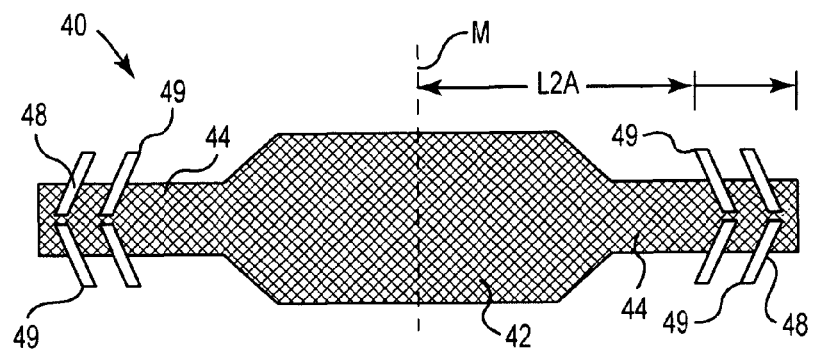
FIGS. 2A, 2B, and 2C illustrate exemplary features of implants and tissue support portions of implants as described.
Figure 2B:
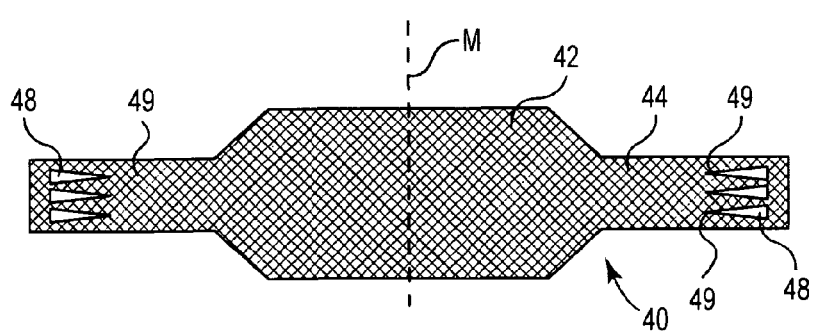
Figure 2C:
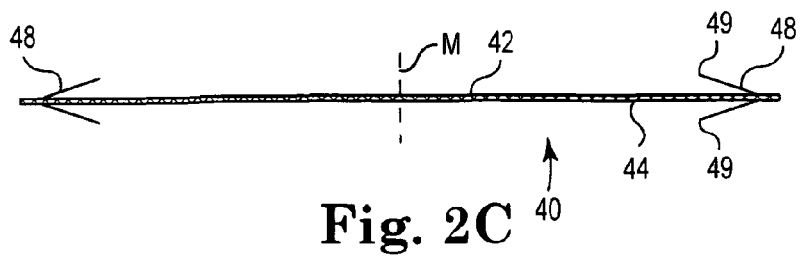

Examples of various exemplary implant embodiments that include tissue fasteners are illustrated at FIGS. 2A, 2B, and 2C.

As shown at FIG. 2A, implant 40 includes tissue support portion 42 and opposing extension portions 44. Tissue support portion 42 and extension portions 44 are an integral mesh. Tissue fasteners 48 are structures added to the mesh of extension portions 44, e.g., by thermoforming a polymeric material (e.g., polypropylene) in the illustrated shape, or by other attachment such as by adhesive attachment. Tissue fasteners 48 can be relatively rigid, such as of a polymeric material (e.g., polypropylene). Tissue fasteners 48 are "chevron"-shaped, with ends 49 slanted toward midline "M," in a manner to facilitate movement of extension portion 44 through tissue in one direction (away from midline "M"), and resulting in a resistant force against movement in the opposite direction once placed. Implant 40 can be placed in a patient to support a urethra, above midline "M" (a location at the middle of tissue support portion 40), and extension portions 44 can be extended to supportive tissue such as at an obturator foramen or tissue or fascia located between the urethra and an obturator foramen. The range of distance (length L2A) between tissue fasteners 48 and midline "M" can be a useful length, such as a length in the range from 3 to 7 centimeters.

FIG. 2B shows (top view) an alternate implant 40, having similar features but alternate versions of tissue fastener 48. FIG. 2C is a side view of FIG. 2B.

According to various embodiments of implants described herein, an implant can include multiple pieces that are adjustably connected together by an adjusting engagement. A "multi-piece" implant refers to an implant that includes a "support portion piece" and one or multiple "extension portion piece" as separate pieces of the implant. An extension portion piece can be separate from a support portion piece, and the two pieces can be connected through an adjustable engagement. The support portion piece includes a tissue support portion.

An adjusting engagement may be for example a one-way adjusting engagement or a two-way adjusting engagement, that allows a portion or a segment of an implant to be moved relative to another portion or segment, and adjusted as to length, tension, or positioning. Examples of adjusting engagements are described, for example, in Applicant's copending U.S. patent application Ser. No. 12/308,436, filed Dec. 15, 2008, entitled SURGICAL IMPLANTS AND TOOLS FOR TREATING PELVIC CONDITIONS, and U.S. patent application Ser. No. 12/669,099, filed Jan. 14, 2010, entitled PELVIC FLOOR TREATMENTS AND RELATED TOOLS AND IMPLANTS, the entireties of which are incorporated herein by reference. As an example, an extension portion piece can be attached to a support portion piece at an adjusting engagement to allow adjustment of a length of extension portion.

Some adjusting engagements can allow two-way movement of one piece relative to another piece (e.g., a "two-way" adjusting engagement). This type of adjusting engagement allows movement of a segment of implant (e.g., of a segment or portion of an extension portion piece) in two directions through an adjusting engagement. The force needed to move the segment of implant in one direction is substantially equal to the force needed to move the segment in the opposite direction, and, optionally, the two-way adjusting engagement does not substantially hinder the movement of a segment of implant through the adjusting engagement with frictional surfaces such as extensions (e.g., "teeth") extending into an aperture through which the segment of implant is moved. As an example, a two-way adjusting engagement may include an open (smooth) aperture that may be circular, oval, square, elongate, or rectangular, such as in the form of a circle, slit, or slot, etc. The aperture may optionally be reinforced by a reinforced perimeter of a shape that is similar to the aperture, such as by a fabric or a polymeric material such as a grommet (e.g., a "loose grommet" or "eyelet"), which may be circular, square, rectangular, or of any desired shape. The reinforced perimeter (e.g., grommet) defines a reinforced aperture through which a segment of implant can pass relatively freely and with the same resistance two different directions.

Other adjusting engagements may allow for one-way adjustment such as shortening of a length of an extension portion. These adjusting engagements can be referred to as "one-way" adjusting engagements, and allow adjustment of a length of an implant portion (e.g., extension portion) in one direction and not (or not easily) in an opposite direction. An exemplary one-way adjusting engagement can include an aperture through which a segment of implant (e.g., a portion of an extension portion piece) can extend, and one or multiple surfaces (e.g., extensions or teeth) that frictionally engage the segment of implant passing therethrough, e.g., by extending into or toward the aperture or otherwise contacting the segment of implant to inhibit movement of the segment of implant relative to the adjusting engagement. The one-way engagement can preferentially allow movement of the segment of implant through the aperture in one direction while inhibiting or preventing movement of the segment of implant in an opposing direction.

In use of a tissue support portion that includes a one-way adjusting engagement such as a round or rectangular grommet, a tissue fastener (e.g., a self-fixating tip) at one end of an extension portion is placed at tissue as desired, and the second (loose) end of the extension portion piece is passed through the one-way adjusting engagement. The engagement is adjusted to place the support portion piece at a desired position (length) of the extension portion piece to provide desired support to a urethra. The one-way adjusting engagement moves easily along the extension portion piece in a direction that tightens the implant against urethra tissue, and does not move easily in the opposite direction. Once placed in position below the urethra and tightened as desired, the support portion piece is prevented from moving along the extension portion piece in the direction to reduce support of the urethra. The extension portion piece may optionally be smooth, without any frictional surface, or may alternately include bumps, detents, teeth, a jagged surface, or other frictional or mechanical structure to engage opposing structure at a surface of an aperture of the one-way adjusting engagement.

In other embodiments, an extension portion piece may engage a support portion piece at a two-way adjusting engagement, and another adjusting engagement (e.g., a one-way adjusting engagement) can be used to secure final positioning of the two pieces. As an example, a segment of an extension portion piece may extend through a two-way adjusting engagement located at a support portion piece. Because the two-way adjusting engagement allows adjustment in two directions, a second adjusting element can be used to fix the extension portion piece in place relative to the support portion piece. For example, an adjusting engagement in the form of a one-way grommet can be placed on the loose end of the extension portion piece. The one-way grommet can be used to secure the positioning of the extension portion piece and support portion piece after adjustment.

In use, the tissue fastener (e.g., a self-fixating tip) located, e.g., on an extension portion, is placed at tissue as desired, and the second (loose) end of the extension portion piece is passed through the two-way adjusting engagement. The engagement is adjusted to place the support portion piece at a desired position (length) of the extension portion piece. A second adjusting engagement, e.g., a one-way grommet, is slid onto the loose end of the extension portion piece and slid along the extension portion piece to a location at the two-way adjusting engagement. The one-way adjusting engagement moves easily along the extension portion piece in the direction toward two-way adjusting engagement, and does not move easily in the opposite direction. Once placed in position near the two-way adjusting engagement of the support portion piece, the support portion piece is prevented from moving along the extension portion piece in the direction of the one-way adjusting engagement.

Figure 3B:
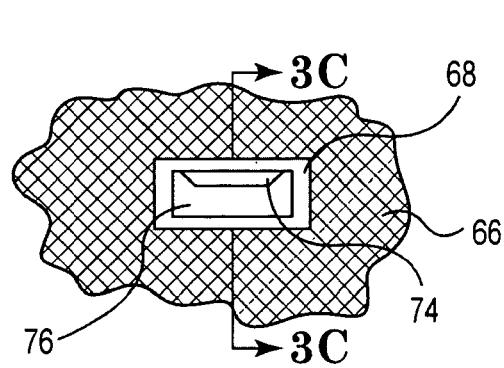
Figure 3C:
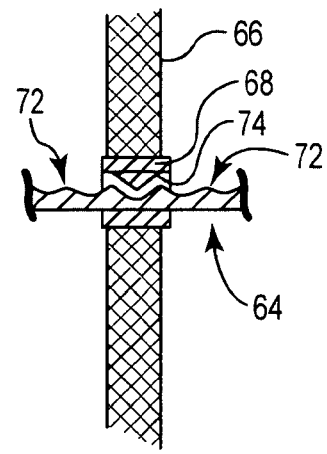

An example of a multi-piece implant is shown at FIG. 3. Kit or assembly 60 includes support portion piece 62 and two extension portion pieces 64. Support portion piece 62 includes tissue support portion 66 and may optionally include or be considered to include an amount of an extension portion. Grommets 68 may be one-way grommets or two-way grommets, and are illustrated to be rectangular, to accommodate extension portion pieces 64, also of rectangular cross section. Grommets 68 are illustrated as "two-way" grommets with frictional surfaces; the adjusting engagement is frictional and opposes movement in either direction, but opposes movement in each direction by the same amount and does not prevent movement in either direction. Aperture 76 is rectangular, is sized to allow passage of extension portion piece 64, and includes extension 74 (see FIGS. 3B and 3C), which extends into aperture 76 to frictionally engage surfaces of extension portion piece 64. Distal ends of extension portion pieces 64 include self-fixating tips 70 for placement at soft supportive tissue such as fascia, muscle, or other tissue of a pelvic region or an obturator foramen. Extension portion pieces 64 are elongate, non-mesh, plastic strips having any cross sectional shape or form (rectangular, as illustrated), and having frictional engagements 72 along a length, in the form of lateral ridges, teeth, or jagged edges, that frictionally interact with extension 74 of rectangular grommet 68. FIG. 3B shows a detailed illustration of rectangular grommet 76 and extension 74 into aperture 76. FIG. 3C shows extension portion piece 64 placed within aperture 76, with frictional engagement between engagements 72 of extension portion piece 64, and grommet extension 74.

Another example of a multi-piece implant is shown at FIG. 4. Kit or assembly 80 includes support portion piece 82 and two extension portion pieces 84. Support portion piece 82 includes tissue support portion 86 and may optionally include or be considered to include an amount of an extension portion. Grommets 88 are illustrated to be two-way grommets (but may alternately be one-way grommets) and are illustrated to be round (e.g., circular), to accommodate the round (e.g., circular) non-mesh portion 85 of extension portion pieces 84. Aperture 86 is round, is sized to allow passage of extension portion piece 84, and as illustrated is a two-way grommet. Distal ends of extension portion pieces 84 include self-fixating tips 90 for placement at soft supportive tissue such as fascia, muscle, or other tissue of a pelvic region or an obturator foramen. Extension portion pieces 84 are elongate strips that include mesh portion 87 and non-mesh portion 85 in the form of a plastic "rod" having a round (e.g., circular) cross section. As illustrated, non-mesh portions 85 are relatively smooth and do not include frictional engagements to frictionally interact with grommet 88.

FIG. 4 also illustrate adjusting tool 92 as an optional component of kit 80. Embodiments of the invention that include multi-piece implants can involve an adjusting tool for simultaneously contacting two surfaces of an implant, especially two spaced surfaces of a support portion piece, to manipulate or stabilize the support portion piece, to allow adjustment of extension portion pieces relative to the support portion piece. Preferred tools can include two adjusting surfaces that are capable of concurrently (e.g., simultaneously) contacting two spaced surfaces of a support portion piece, each of the two surfaces of the support portion piece being part of, at, or adjacent to a component of an adjustable connection, such as at or proximal to a surface of a grommet.

An adjusting tool can include any useful structure to support the adjusting surfaces of the adjusting tool, such as a handle (optional) at a proximal end, a shaft extending from the handle, or alternate forms of support for the adjusting surfaces. An adjusting surface can be any surface that can contact or otherwise engage a surface of an implant. Optionally and preferably an adjusting surface can be a structure that defines an aperture, slot, or slit, that is sized to engage an extension portion piece (e.g., a proximal end of an extension portion piece) by threading or otherwise passing the extension portion piece through the aperture, slot, or slit, to guide or otherwise engage the extension portion piece during adjustment. Adjusting surfaces of an adjusting tool can be spaced from each other by a distance that will allow simultaneous contact with two locations on opposing sides of an implant (e.g., at opposite ends of a tissue support portion) during use of the adjusting tool to adjust the placement of the implant relative to extension portion pieces and relative to urethral tissue being supported. For example, adjusting surfaces may be located on a line that is perpendicular to an axis of a shaft of an adjusting tool, or that is perpendicular to a line parallel to an axis of a shaft of a tool, and may be spaced by a distance in the range of 0.5 to 6 centimeters, such as a distance in the range from 2 to 5 centimeters.

In certain embodiments, each of two adjusting surfaces can be located at an end of a single or of two shafts extending from a handle. In particular embodiments a single shaft may extend from a handle, two separate tines or extensions can extend in different directions from the single shaft, and one adjusting surface can be at an end of each tine (or "extension"). For example, an adjusting tool may include a handle, a single shaft, and a "yoke" fixed or movably located at a distal end of the shaft; the yoke can extend in two directions from the shaft and can include one adjusting surface at the end of each extension. A line that connects the adjusting surfaces may be located to intersect a longitudinal axis of the shaft (the shaft, shaft extensions, and adjusting surfaces are contained in a single plane), or, in alternate embodiments, a line that connects the adjusting surfaces may be located to not intersect a longitudinal axis of the shaft (the shaft, shaft extensions, and adjusting surfaces are not contained in a single plane).

The adjusting surfaces can optionally be fixed or may be moveable, e.g., relative to a shaft. The adjusting surfaces may be fixed, or may be capable of being moved relative to a shaft in a manner to allow the adjusting surfaces to contact and adjust an implant by contacting opposite ends of the implant (e.g., support portion piece) simultaneously. For example, the adjusting tool may include a handle, a single shaft, and a "yoke" that can be moved along a length of the shaft, the yoke extending in two directions from the shaft and including one adjusting surface at the end of each extension. In one embodiment, the yoke may include a central aperture at a middle or median location between the adjusting surfaces, and the central aperture can engage the shaft to allow movement between the yoke and the shaft. Other embodiments can allow for movement with alternate structures. The yoke may be straight or curved.

The distal end of the shaft may optionally be adapted to contact the urethra during adjustment, for example by having a curved (e.g., concave) surface that approximates or matches the shape of surface of urethra tissue supported by the tissue support portion of the implant being adjusted.

Figure 4A:
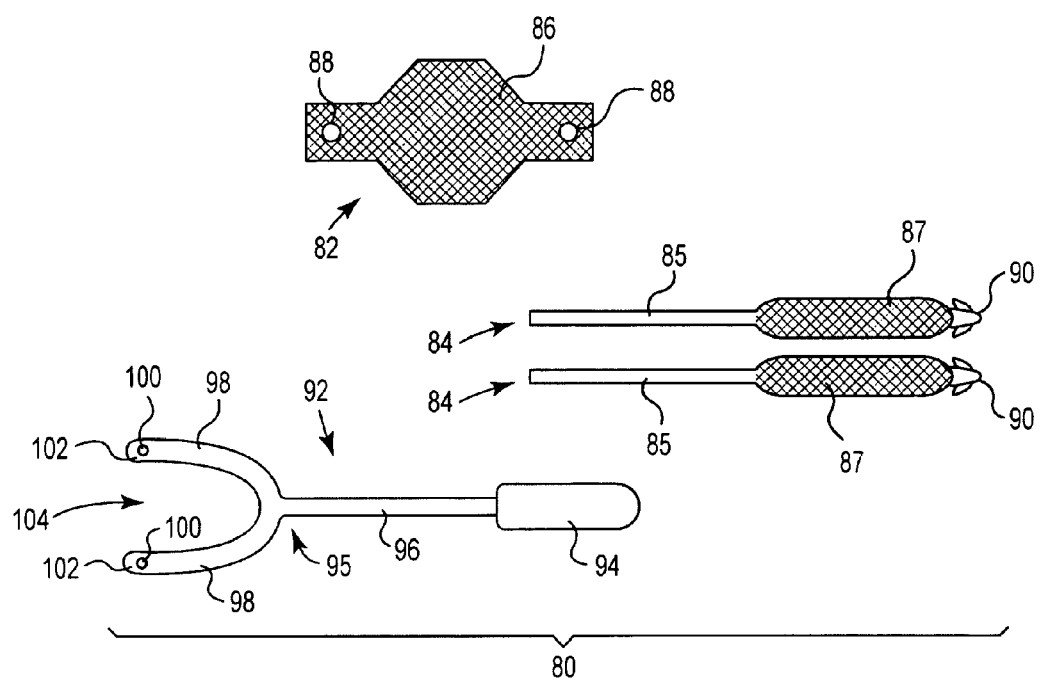
FIGS. 4A, 4D, and 4E illustrates exemplary features of systems, implants, adjustable connections, pieces of multi-piece implants, and adjusting tools, as described.

Referring to adjusting tool 92 at FIG. 4A, a top view, tool 92 includes handle 94, shaft 96 extending from a proximal shaft end at handle 94, to junction 95, where the distal end of shaft 96 meets yoke (alternately opposing "yoke extensions") 98, extending in two directions away from shaft 96. Yoke 98 includes opening (or "gap") 104 between its opposing extensions that allows yoke 98 to be placed below a urethra with opposing yoke extensions along opposite sides of the urethra, i.e., to straddle the urethra. Each of the two distal ends of each yoke extension 98 includes adjusting surface 102 that surrounds aperture 100, and that can contact a surface of an implant such as a grommet, a mesh surface, mesh adjacent to a grommet, or another surface that is part of an adjusting mechanism or that is adjacent to an adjusting mechanism.

Figure 4B:
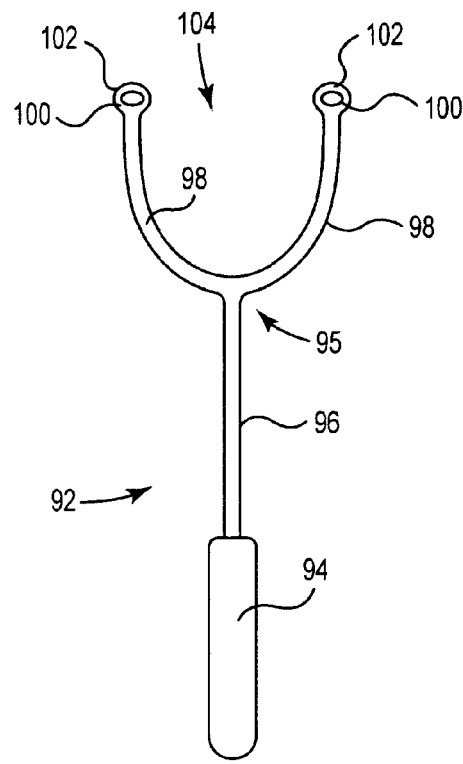
FIGS. 4B, 4C, and 4F illustrate exemplary features of embodiments of adjusting tools, as described.
Figure 4C:
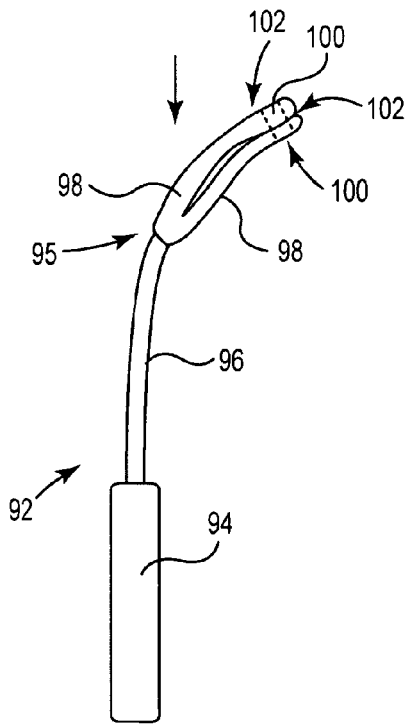
Figure 4D:
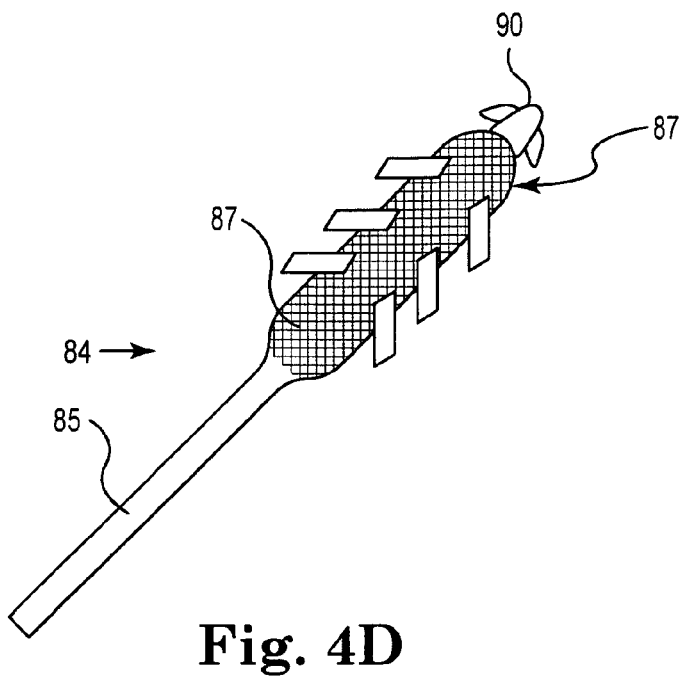
Figure 4E:
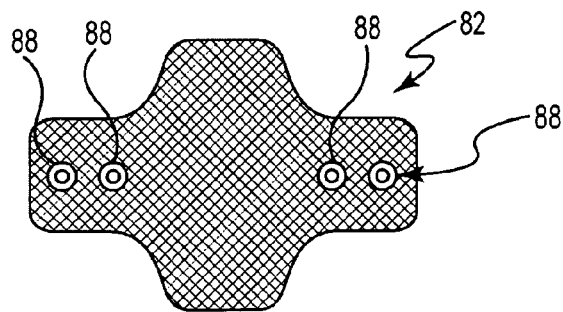
Figure 4F:
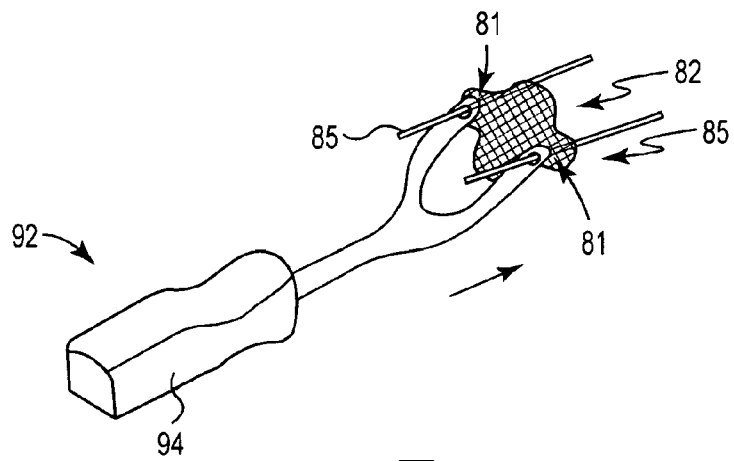

FIGS. 4B, 4C, and 4F illustrate a top view, side view, and side perspective view, respectively, of adjusting tool 92. FIG. 4F additionally shows adjusting surfaces 102 simultaneously engaging two spaced-apart surfaces (81) of support portion piece 82, each surface at a different end of support portion piece 82, to adjust a position of support portion piece 82 relative to non-mesh portions 85.

FIG. 4D shows a variation of extension portion piece 84, this variation including tissue fasteners in the form of "sidebarbs" located at edges of mesh portion 87.

FIG. 4E shows a variation of support portion piece 82, this variation including multiple grommets 88 a opposing ends of support portion piece 82, to allow for placement of extension portion pieces at different locations of support portion piece 82, e.g., to accommodate different sizes or anatomical features of a patient.

Figure 5A:
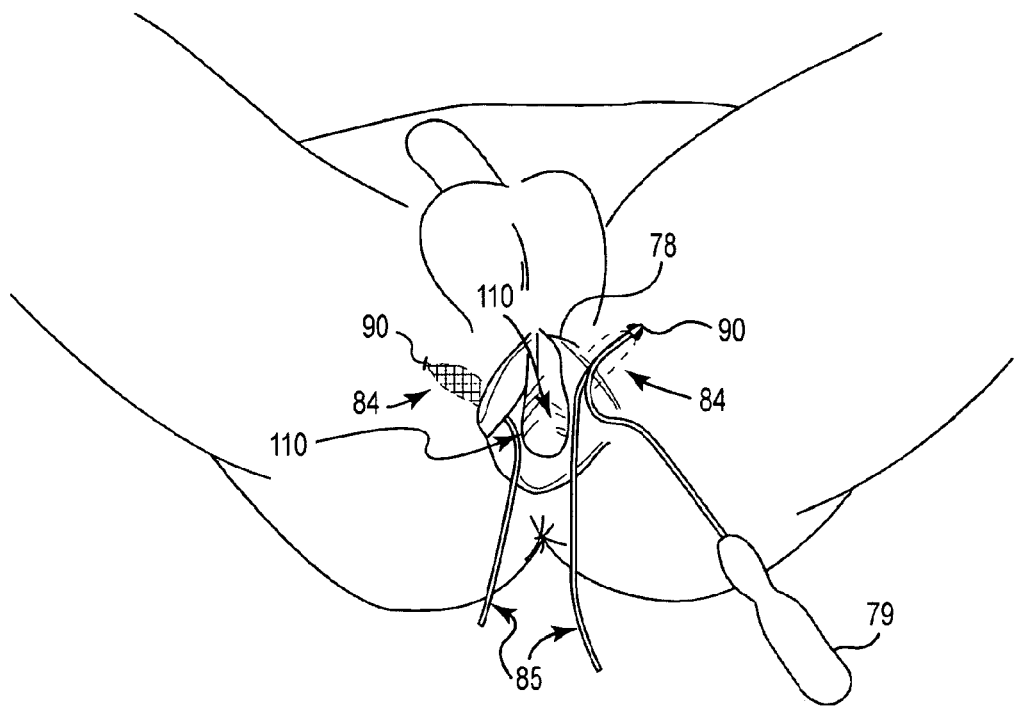
FIGS. 5A, 5B, 5C, and 5D illustrate features of exemplary methods of treating incontinence, as described, and related anatomy.
Figure 5B:
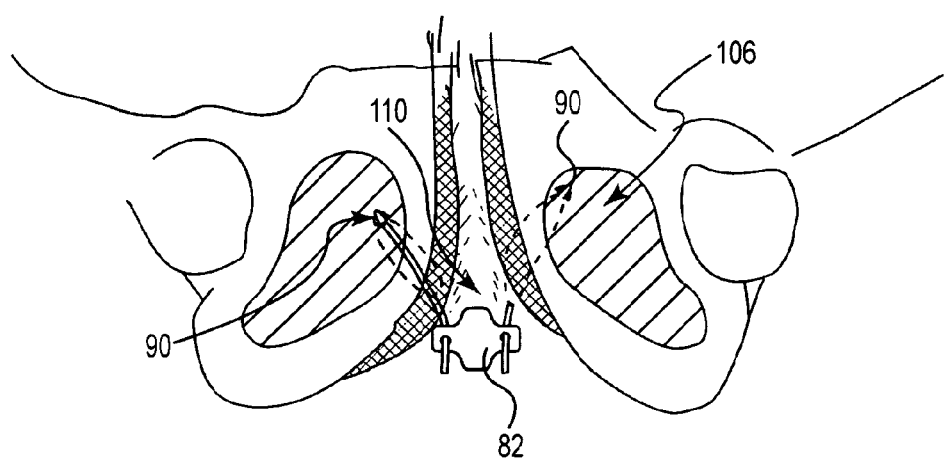

FIGS. 5A and 5B show anatomy related to the use of a multi-piece implant such as implant shown at FIG. 4A, for treating urethral incontinence in a male patient. Medial (perineal) incision 78 allows access to tissue below a urethra (110), such as a bulbar urethra (as described, optionally after dissecting through bulbospongiosus muscle to reach corpus spongiosum tissue). Distinct from certain procedures referred to as "transobturator" methods, no lateral incisions are required at left and right inner thigh positions, adjacent to the patient's opposing left and right obturator foramen.

Still referring to FIGS. 5A and 5B, one or two insertion tools, e.g., having a curved or helical needle portion, are used to place a tissue fastener or self-fixating tip (90) at tissue of an obturator foramen (106, e.g., muscle). Each tissue fastener 90 is at a distal end of an extension portion piece (84) of an implant, and a tissue support portion (82) can be placed onto the extension portion pieces, then moved and adjusted toward urethra 110 to support the urethra to improve continence.

Figure 5C:
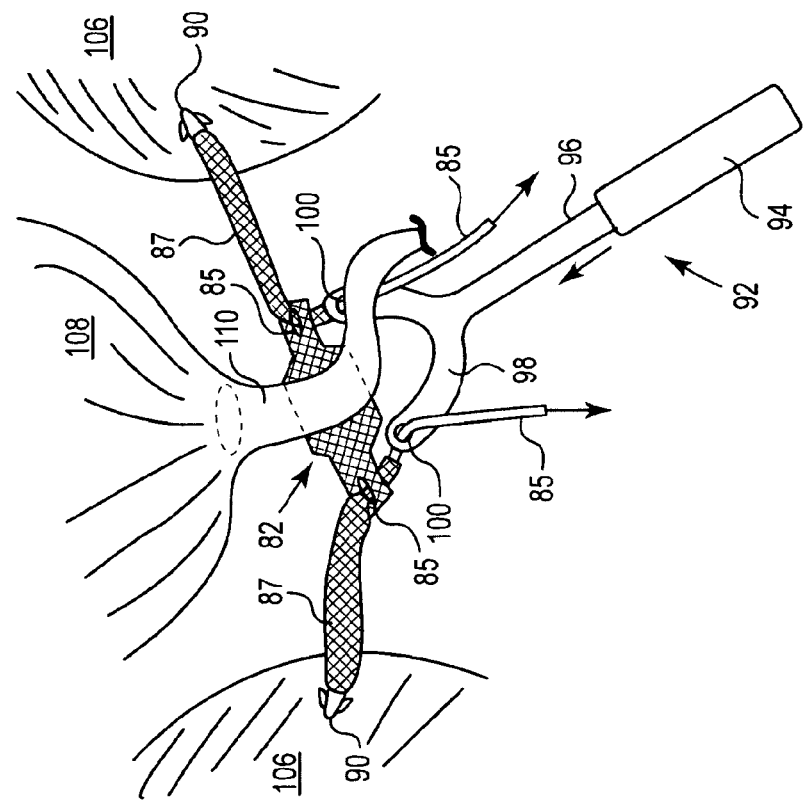
Figure 5D:
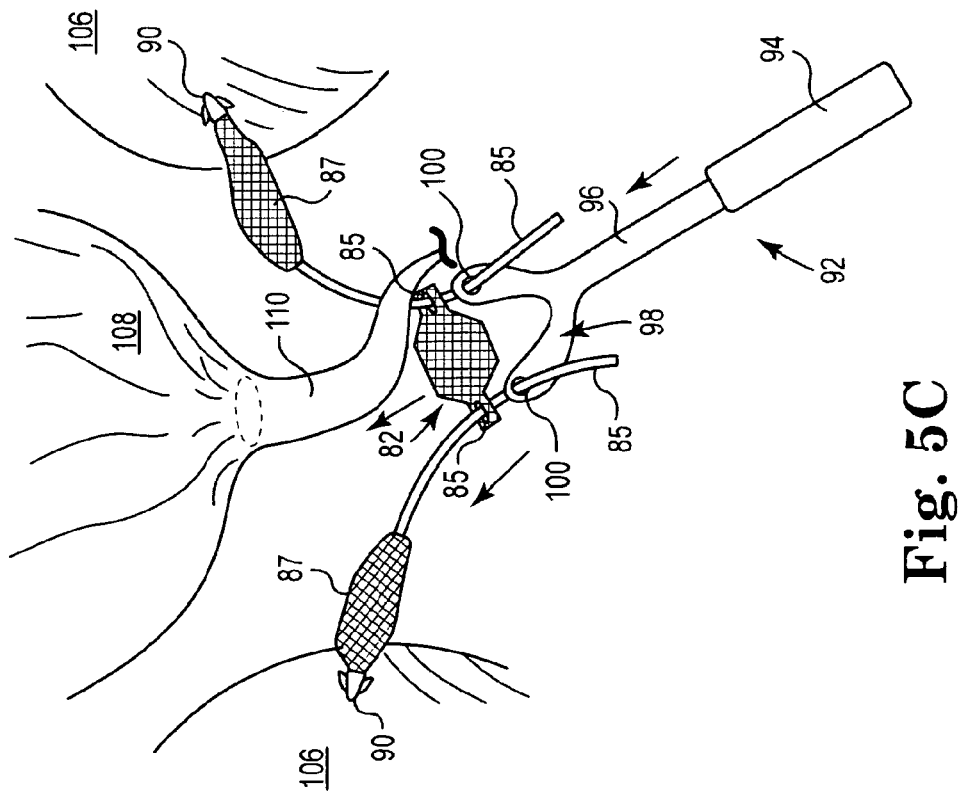

As further illustrated at FIGS. 5C and 5D, non-mesh portions 85 of each extension portion piece 84 are threaded through an aperture of grommet (or other adjusting engagement) 85. Before or after these placements, self-fixating tips 90 are placed at supportive tissue, such as opposing obturator foramen 106 (as illustrated), alternately at adjacent fascia or at fascia more proximal to urethra 110. Support portion piece 82 is placed below urethra 110 (shown with bladder 108). After initial placement, the position of support portion piece 82 relative to urethra 110, and relative to extension portion pieces 84, can be adjusted as follows. Proximal ends of non-mesh portions 85 are passed through each of two apertures 100; adjusting tool 92 and support portion piece 82 are moved toward the patient, to move to support portion piece 82 into position to support the urethra (see FIG. 5B). For final adjustment, adjusting surfaces 102 of yoke 98 can be moved to contact support portion piece 82, e.g., at opposed ends of a tissue support portion, e.g., adjacent to grommets 88; further movement of adjusting tool 92 in the direction of bladder 108 causes mesh portion 87 of each extension portion piece 84 to pass into grommets 88 and become tensioned to support portion piece 82 and urethra 110. If necessary to achieve desired adjustment and tension, yoke 98 can be moved to place opposing extensions in positions lateral to urethra 110. Adjusting surfaces 102 are able to contact both of grommets 88 at once, simultaneously, to allow support portion piece 82 to be advanced uniformly at both ends of a tissue support portion, and uniformly relative to both sides of a patient and a urethra.

Figure 6A:
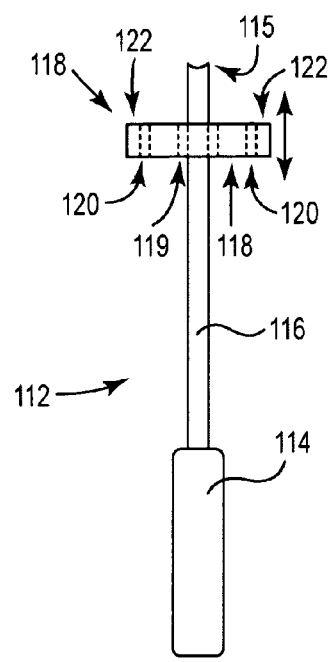
FIGS. 6A and 6B illustrate exemplary features of embodiments of adjusting tools, as described.

Another embodiment of an adjusting tool is shown at FIG. 6A. Adjusting tool 112 includes handle 114 (which is optional), shaft 116 extending longitudinally from a proximal shaft end at handle 114 to distal shaft end 115. Yoke (alternately two yoke extensions) 118 extends in two directions (laterally) away from shaft 116. Yoke 118 includes apertures 120 at ends of opposing extensions 118, and adjusting surface 122 that surrounds each aperture 120. Yoke 118 also includes central aperture 119 (in dashed lines), which fits over shaft 116, allowing yoke 118 to move (as indicated by arrows) longitudinally along a length of shaft 116. Distal shaft end 115 includes a concave, curved surface that can be placed against urethra or associated tissue to allow tool 112 to be used to: 1) adjust a position of a urethra (approximate the urethra) by placing distal shaft end 115 in contact with urethra or associated tissue; and 2) during the same procedure, using yoke 118 optionally by moving yoke 118 longitudinally (e.g., distally) along a length of shaft 116, to place adjusting surfaces 122 to contact two different and spaced-apart surfaces of an extension portion piece (e.g., opposite ends of a tissue support portion) simultaneously and adjust a position of the extension portion piece (or tissue support portion) relative to a urethra and relative to extension portions or extension portion pieces.

Figure 7:
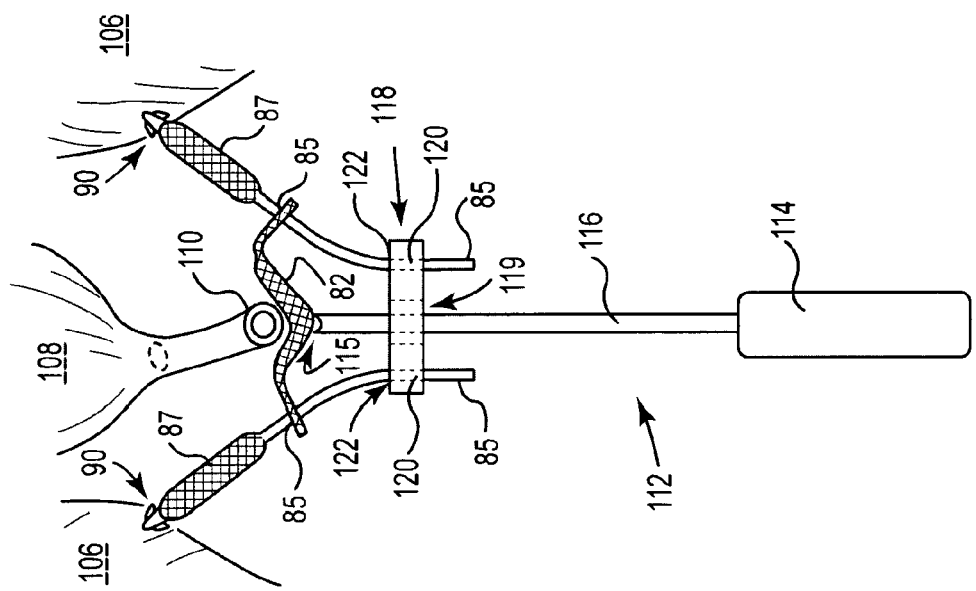
FIG. 7 illustrates features of exemplary methods of treating incontinence in a patient, as described, and related anatomy

In use as illustrated at FIG. 7, a portion of an extension portion (e.g., proximal non-mesh portion 85 of extension portion piece 84, as illustrated) is threaded through an aperture of grommet (or other adjusting engagement) 85. Before or after these placements, self-fixating tips 90 are placed at supportive tissue such as opposing obturator foramen 106 (alternately at fascia). Support portion piece 82 is placed below urethra 110. After initial placement, the position of support portion piece 82 relative to urethra 110, and relative to extension portion pieces 84, can be adjusted as follows. Proximal ends of non-mesh portions 85 are passed through each of two apertures 120 of moveably yoke 118 of adjusting tool 112. Adjusting tool 112 and support portion piece 82 are moved toward the patient, e.g., by movement of yoke 118, adjusting tool 112, or both, to move support portion piece 82 into position to support urethra 110. Distal shaft end 115 of shaft 116 can be used to support or approximate urethra 110 and support portion piece 82. Thus, a step of the method can include approximating urethra 110 by supporting urethra 110 (optionally through support portion piece 82) using distal shaft end 115 of adjusting tool 112, such as by contacting distal shaft end 115 with urethra 110 (optionally through support portion piece 82) to temporarily support or approximate urethra 110 while positioning and adjusting the position of the implant. For final adjustment, adjusting surfaces 122 of yoke 118 can be moved longitudinally (proximally or distally) along a length of shaft 116 to contact support portion piece 82, e.g., at or adjacent to grommets 88 (not shown), and movement of yoke 118 distally in the direction of bladder 108 can cause a mesh portion 87 of each extension portion piece 84 to pass into grommet 88 and become tensioned to support support portion piece 82 and urethra 110. Adjusting surfaces 102 are able to contact both of grommets 88 at once, simultaneously, to allow support portion piece 82 to be advanced uniformly on both ends, and uniformly relative to both sides of a patient and a urethra.

Figure 6B:
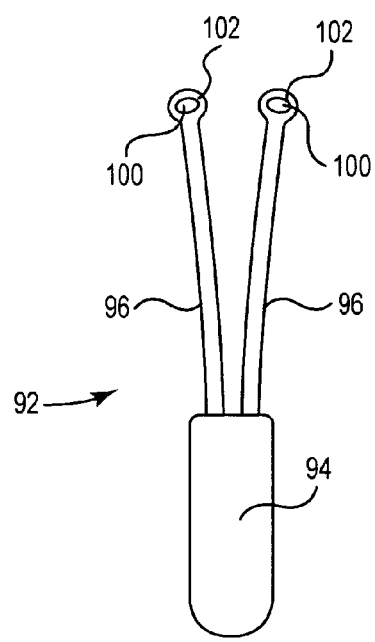

Examples of another embodiment of an adjusting tool is illustrated at FIG. 6B. Adjusting tool 92, a top view, includes handle 94, two shafts 96 each extending from a proximal shaft end at handle 94. Each distal end of shafts 96 includes adjusting surface 102 that surrounds aperture 100.

Implants as described may be placed to support a urethra of a male or a female patient, by methods that involve two opposing transobturator tissue paths, as described a Applicant's U.S. Pat. No. 7,070,556 and Applicant's copending United States Patent Publication Number US 2006-0287571-A1, each of which is incorporated herein by reference in their entireties. These "transobturator" methods generally involve making two lateral incisions at the inner thigh, each near a patient's obturator foramen, and a third, medial incision at the perineum of a male patient and at vaginal tissue of a female patient. An implant (as described herein) is implanted between the medial incision and the two lateral incisions, with opposing extension portions of the implant traversing each obturator foramen.

The urethral implant may be placed using one or more tools by installing extension portions of the sling between the medial and the lateral incisions and passing through the obturator foramen. The extension portion may be passed through the tissue path by initially inserting an insertion tool (needle) at a medial incision and advancing the insertion tool toward an obturator foramen or through an obturator foramen and to an exit point at a lateral incision (this method may sometimes be referred to as an "inside-out" tissue path trajectory, because the insertion path of the insertion tool is from the medial incision to the obturator foramen or to the lateral incision). Alternately, an extension portion may be placed by initially placing an insertion tool through an external, medial incision; advancing the insertion tool medially through an obturator foramen and to a medial incision; connecting the insertion tool to an end of an extension portion; and retracting the insertion tool to pull the extension portion into place in the transobturator tissue path (this method may sometimes referred to as an "outside-in" tissue path trajectory, because the insertion path of the insertion tool is from the lateral incision to a medial incision).

In more detail, an exemplary method includes steps of creating a medial incision at the exterior perineum (in a male), creating an external lateral incision substantially adjacent the patient's obturator foramen, providing an elongate surgical instrument such as an instrument that comprises first and second regions, the instrument having substantial structure in two or three dimensions, and providing an implant for treating the incontinence (a urethral sling). The two- or three-dimensional needle may be passed between the incisions, and then the implant can be associated with the instrument, e.g., at the end of the two- or three-dimensional region. For example, the needle may be passed from the lateral incision through the obturator foramen and to the medial incision, and the implant can be associated with the tip of the needle extending from the medial incision. The needle can then be pulled back through the incisions to pull the extension portion of the implant from the medial incision, through the obturator foramen, and to the lateral incision. Alternately, the implant can be associated with the needle before passing the needle between incisions. The needle, with the extension portion of an implant associated with the needle tip, may then be passed between incisions, such as from the medial incision, through the obturator foramen, and then through the lateral incision. This can be done on both the right side and the left side of the patient.

According to certain preferred methods of treating incontinence in a male, using implants as described, an implant can be placed below a urethra to contact tissue of a corpus spongiosum (by dissecting bulbospongiosus muscle), and the urethra can be approximated to improve continence without requiring the urethra to be compressed.

As described more specifically in US 2006-0287571-A1, according to exemplary embodiments of treating incontinence using any of the implants or tools described herein, a tissue support portion of an implant can be placed in a position to approximate and support a urethra, optionally and preferably without placing compressive forces on the urethra, to effect improved continence (e.g., in a male patient). Preferably, a tissue support portion can be placed to contact tissue of a corpus spongiosum and is tensioned to cause approximation of the corpus spongiosum and urethra in a proximal direction (meaning in this instance, toward a bladder). Accordingly, embodiments of the invention generally, in a male patient, can relate to placement of a tissue support portion at a location that supports and is tensioned to proximally (toward a bladder) re-position a urethra. The implant can be tensioned to cause the urethra—especially the posterior portion of urethra above a perineal membrane—to be moved from an abnormal (e.g., prolapsed or descended) position to a position of normal healthy urethral tissue capable of being fully coapted upon contraction of the rhabdosphincter. Alternate methods can cause compression of the urethra, but compression is not required in methods that result in approximation of the urethra to improve continence.

According to these embodiments, a method of surgically installing a urethral implant can include providing a medial incision at the perineum of a male patient to expose bulbospongiosus muscle, optionally and preferably dissecting through bulbospongiosus muscle to expose corpus spongiosum, and placing a tissue support portion of the implant to contact the corpus spongiosum tissue. Optionally the tissue support portion can be fixed to the corpus spongiosum, such as by use of a medical attachment in the form of a suture, staple, adhesive, or the like. The implant can be adjusted, tensioned, etc., e.g. based on the use of an adjusting engagement, an adjustment tool, or both, to approximate the urethra to improve continence, and tension can optionally and preferably maintained chronically.

In alternate implantation methods in a male or female patient (still optionally and preferably in a male patient, placing a tissue support portion in contact with corpus spongiosum, and approximating a urethra without a requirement for compression of a urethra), an implant can be inserted through a medial (perineal or vaginal) incision and an extension portion of the implant can be attached to tissue of an obturator foramen, or to tissue (e.g., fascia) that lies between a urethra and tissue of an obturator foramen. According to such methods, a tissue fastener such as a self-fixating tip at a distal end or distal portion of an extension portion can be engaged at a distal end of an insertion tool (e.g. a curved elongate needle). The insertion tool can be used to place the tissue fastener and extension portion through a medial incision (of a male or female patient) and extend the tissue fastener and extension portion in a direction of an obturator foramen, e.g., to tissue of the obturator foramen or to tissue between a urethra and an obturator foramen. Features of the inventive methods, implants, and tools that are described herein can be incorporated into such a technique, such as placement of the urethral sling below a urethra at a tissue of a bulbospongiosus muscle or a corpus spongiosum, approximation of the urethra to improve continence (without the need for compression of the urethra), etc., use of an implant that includes adjustable engagements (and steps of adjusting the implant), use of an adjustment tool. This method avoids the need for lateral incisions at the inner thigh and adjacent to each opposing obturator foramen.

Embodiments of a transobturator method, e.g., in a male patient, can involve insertion needles that pass between a lateral incision and medial incision using a small-diameter needle. An example of an implant for use in this type method is shown at FIG. 8, showing implant 130 that includes tissue support portion 132 (e.g., having dimensions as described herein), extension portions 134 (sutures as illustrated, and having dimensions as described herein), and small-diameter needles 136. Each small-diameter needle can be of a shape as described to be useful or desired for passing an extension portion of an implant through a transobturator tissue path extending between a lateral incision and a medial incision. The shape may be straight, two dimensionally curved, or three dimensionally curved (e.g., helical).

According to the present description, one or more needle for placing an extension portion at a transobturator tissue path, along some or a portion of a length of the needle, may be of a "small-diameter," e.g., less than 0.09 inch in diameter, preferably less than 0.07 or 0.06 inch in diameter. A small-diameter needle can reduce trauma to tissue, increasing patient comfort and possibly improving cure and recovery rates. The needle may be of a small-diameter along an entire length of the needle, or may be of a small-diameter (as described) at a portion of a leading end of the needle, expanding to a larger diameter at a trailing end of the needle. For example the needle may have a small-diameter, e.g., less than 0.09 inch in diameter, preferably less than 0.07 or 0.06 inch in diameter, along at least one half of its entire length, or along at least three-quarters of its entire length, or along ninety percent of its entire length, or along an entire length between a proximal end and a distal end.

Also, a leading end of the needle can include a tip that is sufficiently sharp to penetrate tissue; such a tip at a leading end of the needle can be defined as a tip that has a radius of curvature of no greater than 0.015 inch, such as a radius of curvature that is no greater than 0.010 inch. Still additionally, the small-diameter needle can preferably be of a length (including curvature, meaning an arc-length of a curved needle) that allows the needle to extend completely between the lateral incision and the medial incision: a leading end of the needle can preferably be extended from the lateral incision or the medial incision, while the trailing end has not yet entered the medial or the lateral incision (respectively). An exemplary length to allow the needle to extend completely between the incisions is a length of at least 4 inches, such as a length in the range from about 3 to about 6 inches (see length "L" of FIGS. 8 and 9).

A small-diameter needle can optionally include a handle at a proximal (trailing) end, and can optionally include an aperture or other mechanism to connect to an extension portion (e.g., suture) at either a leading end or a trailing end.

Figure 9:
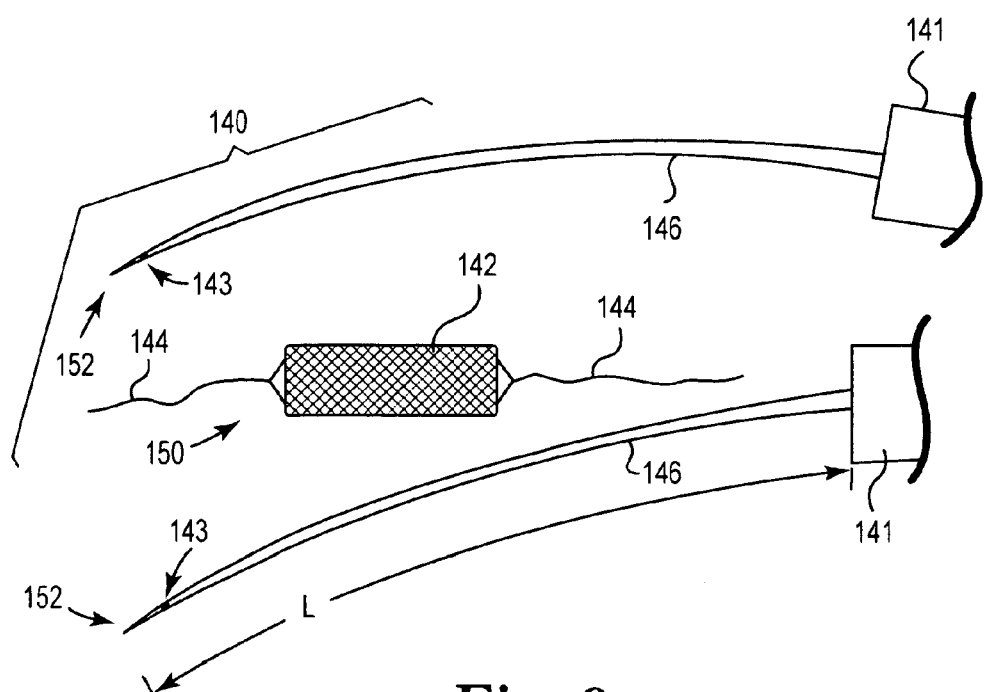
Figure 10A:
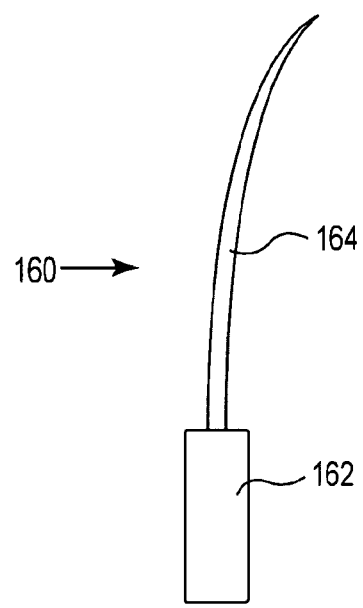
FIGS. 10A, 10B, 11A, and 11B illustrate features exemplary small-diameter insertion tools, as described.
Figure 10B:
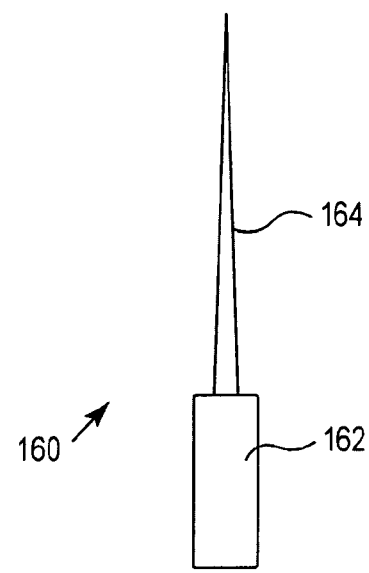
Figure 11A:
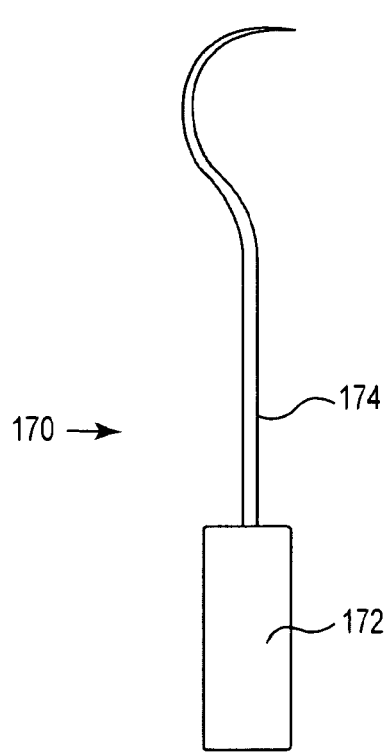
Figure 11B:
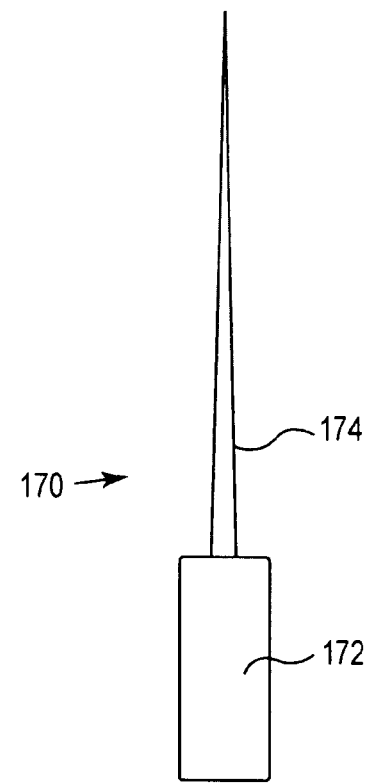

Insertion tools having small-diameter needles are illustrated at FIGS. 8, 9, 10A, 10B, 11A, and 11B. FIG. 10A illustrates a side view of insertion tool 160, with handle 162 and small-diameter needle 164 having a two-dimensionally curved shape. FIG. 10B is a front view. FIG. 11A illustrates a side view of insertion tool 170, with handle 172 and small-diameter needle 174 having a two-dimensionally curved shape that includes multiple curves in different directions. FIG. 11B is a front view. Each of the needles (as illustrated) includes a diameter that is not uniform but that is greater at the proximal end of the needle (toward handle 162, 172) and that decreases moving toward the distal end. Optionally, the diameter could be uniform along the entire length between the proximal and distal ends. Also optionally, each needle can include an aperture at the distal end, to attach a suture.

FIG. 8 shows implant 130 that includes tissue support portion 132 (mesh) and two opposing extension portions in the form of sutures 133. Small-diameter needles 136 are attached (e.g., by knots or other mechanical or adhesive connection, at a proximal end of the needle) at distal ends of each sutures 133. Implant 130 can be useful for treating urinary incontinence, e.g., in a male, by steps that include placing tissue support portion 132 below a urethra or adjacent tissue in a position to support the urethra for improving continence, and extending extension portions 134 along transobturator tissue paths. Implant 130 may be placed to support a urethra, through a medial incision. Each of the two small-diameter needles 136 can be inserted into a medial incision and then passed through an obturator foramen and to an exit point at a location of an inner thigh, adjacent to the obturator foramen. The extension portion may be pulled through the tissue path using the small-diameter needle, by the connection at the trailing end of needle 136 (using an "inside-out" tissue path trajectory). This can be done on the left and the right sides of the patient.

FIG. 9 shows an alternate embodiment of an implant as part of kit 140, including small-diameter needles 146. Implant 150 includes tissue support portion 142 (mesh) and two opposing extension portions in the form of sutures 144. Small-diameter needles 146 are attached at a proximal end of each needle to handles 141. Optionally, and as illustrated, the diameter of each of small-diameter needles increases toward handles 141. Each distal end 152 includes aperture 143, for connecting to a suture 144. Kit 140, including implant 150, can be useful for treating urinary incontinence, e.g., in a male, by steps that include placing tissue support portion 142 below a urethra or adjacent tissue in a position to support the urethra for improving continence, and extending extension portions 144 along transobturator tissue paths. Implant 150 may be placed to support a urethra, through a medial incision. Each of the two small-diameter needles 146 can be inserted into a patient through a skin location at an inner thigh location, adjacent to an obturator foramen, and then passed through an obturator foramen and to the medial incision. The extension portion (suture 144) may then be attached to distal end 152 of small-diameter needle 146, e.g., through aperture 143. Small-diameter needle 146 can then be retracted back through the tissue path to pull suture 144 into place, at a transobturator tissue path (using an "outside-in" tissue path trajectory). This can be done on a left and a right sides of the patient.

In other embodiments of methods for treating incontinence in a male or a female, a method can incorporate the use of a urethra-positioning tool to position a urethra at a location of improved continence function, such as by approximating the urethra toward a bladder or by alleviating prolapse. After using a urethra-positioning tool to position the urethra at a location to improve continence, the method can involve fixing the urethra in place by any useful fixation techniques, such as by use of an implant (as described herein, or otherwise); by use of tissue ingrowth; by use of accelerated tissue ingrowth or scarring based on injection of a substance such as a growth factor, scarring agent, or fibrosis-inducing composition, to reduce elasticity of tissue supporting the urethra; by use of a biologic adhesive; etc. The method may also include adjustment of the location of the urethra following initial placement at the desired location. Optionally, the urethra-positioning tool can include a lumen for draining a bladder during a period over which the tool is installed to allow for fixation of the urethra.

A urethra-positioning tool can be any tool that includes an elongate shaft that is sufficiently rigid (rigid, semi-rigid) to be placed into a urethra, through a meatus, and that can be used to cause the urethra to take on the form (shape) and position of the elongate shaft. The shaft can be, for example, a solid metal or plastic rod, or may be in the form of a catheter that includes a drainage lumen. A handle at a proximal end can facilitate insertion of a distal end into a meatus and placement of the urethra-positioning tool within a urethra to position the urethra at a location of improved continence function.

The shaft can be of a length to extend from a meatus, through a urethra, and to a portion of urethra that is prolapsed and that can be adjusted to improve continence; e.g., a length can be sufficient to extend from a meatus to a bladder neck or a bladder, optionally after a prostate and prostatic portion of a urethra has been removed, e.g., a length in the range from 11 to 22 centimeters, such as from 14 to 21 centimeters. The shaft can be of a shape that is at least partially curved to approximate curves of a urethra, optionally including curves of three portions of the urethra, including the prostatic urethra, the membranous urethra, and the cavernous urethra of the penis i.e., to mimic the shape of a healthy, properly-anatomically-supported, continent urethra, or a portion thereof. For example, a distal portion of the shaft can be of a curved shape that can mimic a healthy, properly-anatomically-supported, continent, membranous or prostatic urethra, and a proximal portion of the shaft can be curved to mimic a cavernous portion of the urethra that passes through a penis; such a shaft will have a "double curve" that mimics a double curve of a healthy urethra or of a continent urethra after removal of a prostate and a portion of the prostatic urethra.

Figure 12A:
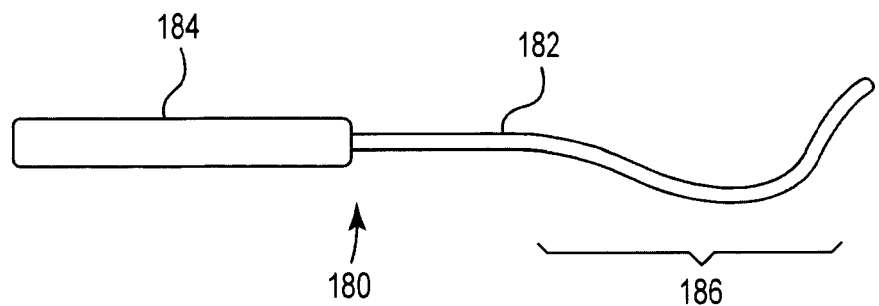
FIGS. 12A, 12B, and 13 illustrate features exemplary urethra-positioning tools, as described.
Figure 12B:
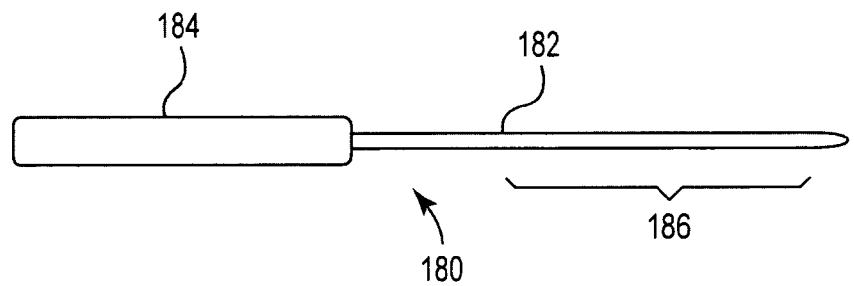

FIG. 12A, 12B show examples of urethra-positioning tools. FIGS. 12A and 12B are side view and top-view (respectively) of tool 180, which includes shaft 182 and handle 184. Distal portion 186 is curved to approximate a shape of a healthy, well-supported and properly-anatomically-positioned prostate.

Figure 13:
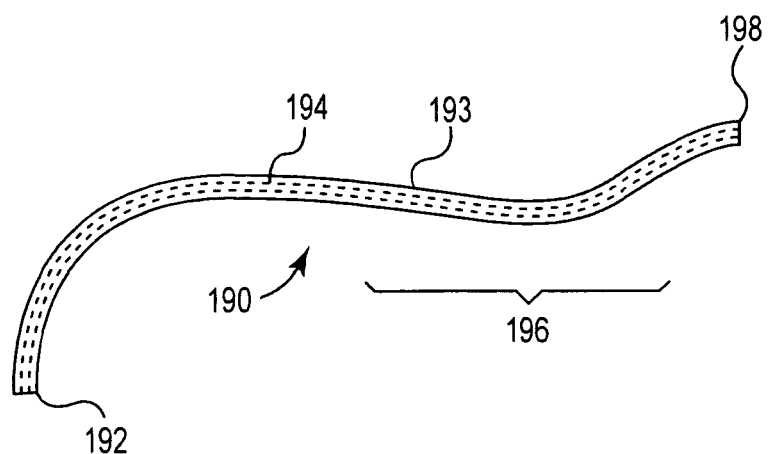

FIG. 13 shows a side view of urethra-positioning tool 190, which includes shaft 193, proximal end 192, distal end 198, and drainage lumen 194 (in dashed lines). Distal portion 196 is curved to approximate a shape of a healthy, well-supported and properly-anatomically-positioned prostate; a proximal portion is curved to mimic a cavernous urethra passing, e.g., through a male penis.

For fixing the urethra in place, after desired positioning using a urethra-positioning tool, examples of useful biologic adhesives include cyanoacrylate, as well as other known adhesives useful in biologic applications. Examples of useful scarring agents, growth factors, and fibrosis-inducing compositions, to reduce elasticity of tissue supporting the urethra, can include hydrocarbon (e.g., petroleum jelly) as described at United States Patent Application Publication Number US 2004/0076653. Some exemplary scarring agents include the category of substances called "sclerosing agents" which are normally used for sclerotherapy. Examples include sodium morrhuate, sodium solution, glucose solution, and crushed pumice. Any of these materials can be injected into tissue surrounding a urethra, such as proximal to urethra submucosa after placing the urethra into a desired position using the urethra-positioning tool—to fix the position of the urethra. The amount of time needed to achieve desired fixation can depend on the type of material injected. A biological adhesive may be capable of fixing tissue in a short time, such as minutes, hours, or days. A growth factor or scarring agent may require days or weeks to achieve fixation, during which time the urethra-positioning tool must remain in place. Optionally, if a urethra-positioning tool remains in place over an extended period, such as many hours, days, or weeks, the tool can include a drainage lumen to allow urine to pass.

Methods that do not place an implant during the fixation step can avoid the use of any incisions, i.e., can be an incisionless method of treating incontinence.

Alternate methods can involve an incision to place a positioning mechanism such as an inflatable item (e.g., an inflatable balloon or pillow) below the urethra, to adjust the position of the urethra during or after a procedure to position and fix the urethra in place. At any time after a procedure of positioning the urethra, with implantation of an inflatable balloon or pillow, the size of the inflatable balloon or pillow can be changed to adjust the position of the urethra. The size of the balloon or pillow may be adjusted, for example, by use of a hypodermic needle to pass a fluid through skin, with no incision, into or out of the inflatable item.

The invention claimed is:

1. An assembly for treating urinary incontinence, the assembly comprising a multi-piece implant comprising a support portion piece, a first extension portion piece, and a second extension portion piece, and an adjusting tool, wherein
the support portion piece comprises a tissue support portion sized and shaped for placement to support a urethra,
the first and second extension portion pieces each comprise a proximal end, a distal end, and a tissue fastener,
the first extension portion piece is adjustably connected to the support portion piece at a first adjustable connection,
the second extension portion piece is adjustably connected to the support portion piece at a second adjustable connection, and
the adjusting tool comprises a shaft, a yoke, and two adjusting surfaces located at the yoke, wherein the two adjusting surfaces are configured for simultaneous engagement with two spaced-apart surfaces of the support portion piece during simultaneous adjustment of a position of the first extension portion piece relative to the support portion piece at the first adjustable connection and a position of the second extension portion piece relative to the support portion piece at the second adjustable connection.

2. An assembly according to claim 1 wherein each of the two adjusting surfaces is adjacent to a slot or aperture adapted to engage the extension portion piece.

3. An assembly according to claim 1 wherein the yoke is stationary relative to the shaft.

4. An assembly according to claim 1 wherein the yoke can be moved relative to a length of the shaft.

5. An implant according to claim 1 wherein the adjustable connection comprises an aperture through which the extension portion piece extends to adjustably connect the extension portion piece to the support portion piece.

6. An implant according to claim 1 wherein the adjustable connection comprises a grommet.

7. An implant according to claim 1 wherein the extension portion piece comprises a tissue fastener.

8. An implant according to claim 1 wherein the implant comprises supportive portions consisting of the tissue support portion and two extension portions.

9. A method of treating urinary incontinence in a patient, the method comprising:
providing an assembly according to claim 1,
creating a medial incision in the patient,
dissecting from the medial incision to tissue below a urethra,
placing the tissue support portion to contact tissue to support the urethra,
placing a distal end of the first extension portion in a tissue path extending toward a first obturator foramen of the patient,
placing a distal end of the second extension portion in a tissue path extending toward a second obturator foramen of the patient,
connecting the first extension portion piece with the support portion piece at the first adjustable connection,
connecting the second extension portion piece with the support portion piece at the second adjustable connection,
engaging the adjusting tool with the spaced-apart surfaces of the support portion piece, and
simultaneously adjusting a position of the support portion piece relative to first and second extension portion pieces.

10. A method according to claim 9, wherein
the implant comprises a left-side extension portion piece connected to the support portion piece at an adjustable connection at a left end of the support portion piece to form a left extension portion, and the method comprises extending the left extension portion to engage supportive tissue at a left side of the patient, and
the implant comprises a right-side extension portion piece connected to the support portion piece at an adjustable connection at a right end of the support portion piece to form a right extension portion, and the method comprises extending the right extension portion to engage supportive tissue at a right side of the patient.

11. A method according to claim 9 wherein the patient is a male patient, the method comprising
exposing bulbospongiosus muscle,
dissecting bulbospongiosus muscle to expose corpus spongiosum, and
placing the tissue support portion to contact the corpus spongiosum.

12. A method according to claim 9, wherein the adjusting tool comprises a shaft and a yoke, the two adjusting surfaces are located at the yoke, the yoke can be moved relative to a length of the shaft, and the method comprises moving the yoke relative to the shaft.

13. In combination, an implant for treating urinary incontinence and an adjusting tool, the implant comprising
a tissue support portion sized and shaped for placement to support a urethra, and
a first and second extension portion, each extension portion extending from an end of the tissue support portion, and
a tissue fastener located at a distal end of each extension portion, wherein each extension portion comprises an adjustable length between the tissue support portion and the tissue fastener
the adjusting tool comprising:
two adjusting apertures, a shaft, and a yoke, the two adjusting apertures located at a distal end of the yoke and configured for simultaneous engagement with the first and second extension portions during simultaneous adjustment of the first and second extension portions relative to the tissue support portion, wherein the yoke is axially movable relative to a length of the shaft.

14. An implant according to claim 13 wherein each of the two extension portions comprises a suture, and the tissue fastener is a self-fixating tip adjustably connected to the suture.

15. A method of treating urinary incontinence in a patient, the method comprising:
provide an implant and adjusting tool according to claim 13,
creating a medial incision in the patient,
dissecting from the medial incision to tissue below a urethra,
placing the tissue support portion to support the urethra,
placing the tissue fastener at the first extension portion in a tissue path extending toward a first obturator foramen of the patient,
placing the tissue fastener at the second extension portion in a tissue path extending toward a second obturator foramen of the patient, and
adjusting the adjustable length between the tissue support portion and the tissue fastener.

\* \* \* \* \*